(12) United States Patent
Balzarini et al.

(10) Patent No.: US 6,818,633 B2
(45) Date of Patent: Nov. 16, 2004

(54) ANTIVIRAL COMPOUNDS AND METHODS FOR SYNTHESIS AND THERAPY

(75) Inventors: Jan M. R. Balzarini, Heverlee (BE); Erik D. A. De Clercq, Lovenjoel (BE); Antonin Holy, Horni Pocernice (CZ)

(73) Assignees: Institute of Organic Chemistry and Biochemistry Academy of Sciences of the Czech Republic (CZ); Rega Stichting v.z.w. (BE)

( * ) Notice: Subject to any disclaimer, the term of this patent is extended or adjusted under 35 U.S.C. 154(b) by 0 days.

(21) Appl. No.: 10/187,166

(22) Filed: Jun. 28, 2002

(65) Prior Publication Data

US 2003/0109499 A1 Jun. 12, 2003

Related U.S. Application Data

(60) Provisional application No. 60/302,212, filed on Jun. 29, 2001.

(51) Int. Cl.[7] .................. A61K 31/662; C07F 9/6512
(52) U.S. Cl. .................. 514/86; 514/88; 544/243
(58) Field of Search .................. 544/243; 514/86, 514/88

(56) References Cited

U.S. PATENT DOCUMENTS

| | | |
|---|---|---|
| 4,659,825 A | 4/1987 | Holy et al. |
| 4,724,233 A | 2/1988 | De Clercq et al. |
| 4,808,716 A | 2/1989 | Holy et al. |
| 5,142,051 A | 8/1992 | Holy et al. |
| 5,208,221 A | 5/1993 | Kim et al. |
| 5,302,585 A | 4/1994 | Yu et al. |
| 5,352,786 A | 10/1994 | Jindrich et al. |
| 5,356,886 A | 10/1994 | Harnden et al. |

FOREIGN PATENT DOCUMENTS

| | | |
|---|---|---|
| EP | 0 269 947 A1 | 6/1988 |
| EP | 0 369 409 A1 | 5/1990 |
| EP | 0 398 231 A2 | 11/1990 |
| EP | 0 434 450 A2 | 6/1991 |
| EP | 0 454 427 A1 | 10/1991 |
| EP | 0 468 119 A1 | 1/1992 |
| EP | 0481 214 A1 | 4/1992 |
| EP | 0 618 214 A1 | 10/1994 |
| EP | 0 630 381 B1 | 12/1994 |
| WO | WO 94/03467 | 2/1994 |
| WO | WO 95/07920 | 3/1995 |
| WO | WO 96/33200 | 10/1996 |

OTHER PUBLICATIONS

Holy et al., "Synthesis of Quaternary 1-[2-(Phosphonomethoxy)Ethyl] Derivatives . . . ", Coll. Czech. Chem. Comm., 1999, Abstract XP-002215043.

Snoeck et al., "Antivaccinia Activities of Acyclic Nucleoside Phosphonate Derivatives . . . ,",Antimocrobial Agents & Chem., Nov. 2002, 46(11):3356–3361.

Wormstadt et al., "Synthesis of Acyclic Nucleoside Phosphonates as Antiviral Compounds", J. Heterocyclic Chem., 2000, 37:1187–11191.

Balzarini et al., "Antiretrovirus Activity of a Novel Class of Acyclic Pyrimidine Nucleoside Phosphonates", Antimicrobial Agents & Chemotherapy, Jul. 2002, 46(7):2185–2193.

Cihlar et al., "Transport of 9–(2–Phosphonomethoxyethyl) Adenine across Plasma Membrane of HeLa S3 Cells . . . " Antimicrob. Agents & Chemo., Jan. 1995, 39(1):117–124.

Daluge et al., "A Novel Carbocyclic Nucleoside Analogue with Potent, Selective Anti–HIV Activity", Abstracts of the 34th ICAAC, Oct. 1994, 1592U89.

Eger et al., "Synthesis of New Acyclic Pyrimidine Nucleoside Analogs as Potential Antiviral Drugs", J. Med. Chem., 1994, 37:3057–3061.

Franchetti et al., "Acyclic Nucleotides Related to Clitocine: Synthesis and Anti–HIV Activity", Nucleosides & Nucleotides, 1995, 14(3–5):607–610.

Holy et al., "Synthesis of Quaternary 1-[2-(Phosphonomethoxy)ethyl] Derivatives of 2,4–Diaminopyrimidine . . . ", Coll. Czech. Chem. Comm., 1999, 64(2):242–256.

Holy et al., "6-[2-(Phosphonomethoxy)Alkoxy]Pyrimidines with Antiviral Activity", J. Med. Chem., 2002, 45:1918–1929.

Holy et al., "Structure–Antiviral Activity Relationship in the Series of Pyrimidine & Purine N-[2-(2-Phospohnomethoxy)Ethyl] . . . ", J. Med. Chem. 1999, 42:2064–2086.

Holy et al., "Phosphonylmethyl Ethers of Nucleosides & Their Acyclic Analogues", ACS Symp. Ser., 1989, 401:57–71.

Holy et al., "Structure–Activity Studies in the Series of Acyclic Nucleotide Analogues", Kem. Ind., 1989, 38(10):457–462.

Primary Examiner—Richard L. Raymond
(74) Attorney, Agent, or Firm—Max D. Hensley

(57) ABSTRACT

Novel compounds are provided having formula (I)

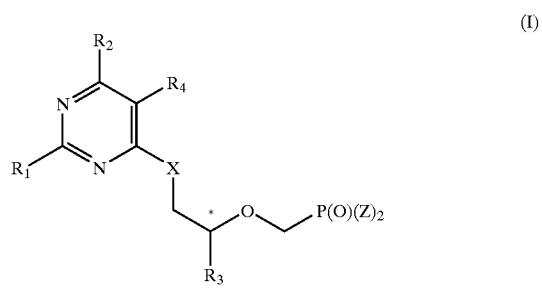

where $R_1$, $R_2$, $R_3$, $R_4$, Z, X and * are defined herein. Also provided are antiviral methods for use and processes for synthesis of the compounds of formula (I).

39 Claims, No Drawings

ANTIVIRAL COMPOUNDS AND METHODS FOR SYNTHESIS AND THERAPY

CROSS REFERENCED TO RELATED APPLICATIONS

This application is based upon U.S. Provisional Application Ser. No. 60/302,212 filed Jun. 29, 2001, and is incorporated herein by reference.

BACKGROUND OF THE INVENTION

FIELD OF THE INVENTION

Acyclic nucleotide analogues containing phosphonate groups are disclosed for example in U.S. Pat. Nos. 4,659,825, 4,808,716, 4,724,233, 5,142,051, 5,302,585, 5,208,221, 5,352,786, 5,356,886, in EP publication numbers 269,947, 481,214, 630,381, 369,409, 454,427, 468,119, 434,450, 618, 214 and 398,231 and in WO 95/07920, WO 94/03467 and WO 96/33200. The teachings of these patents include compounds in which a phosphonate group is linked to a defined purine or pyrimidine base, generally at the 1- or 9-position of the pyrimidine or purine bases, respectively, by way of a 2-(methoxy)propyl group, a 2-(methoxy)ethyl group, a 2-methoxy-3-hydroxypropyl group, or a 2-methoxy-3-fluoropropyl group, known respectively as PMP, PME, HPMP and FPMP purine or pyrimidine compounds. These compounds exhibit antiviral and cytostatic activity.

Daluge et al. (34th Interscience Conference on Antimicrobial Agents and Chemotherapy, Oct. 4–7, 1994) discloses carbovir derivatives in which the 6 position of the purine is substituted with cyclopropylamino, N-cyclopropyl-N-methylamino or N-aziridinyl.

Cihlar et al., "Antimicrobial Agents and Chemotherapy" 39(1):117–124 (1995) disclose $N^6$-aminohexyl-PMEDAP.

Holy et al., "ACS Symp. Ser." 401:57–71 (1989) and Holy, "Kem. Ind." 38(10):457–462 (1989) describe the antiviral activity of certain $N^6$-substituted nucleotide analogues.

Additional phosphonate-substituted pyrimidine analogues are disclosed by Holy et al., "Collect. Czech. Chem. Commun." 64:242–256 (1999), Eger et al., "J. Med. Chem." 37:3057–3061 (1994), Wormstadt et al., "J. Heterocyclic Chem." 37:1187–1191 (2000), and Franchetti et al., "Nucleosides & Nucleotides" 14(3–5): 607–610 (1995). The latter three publications have a phosphonate-containing side-chain linked via a 6-N substituent of 2,4-disubstituted pyrimidine.

OBJECTS OF THE INVENTION

It is an object of this invention to provide compounds having antiviral activity, in particular against RNA or DNA viruses such as HIV, HBV or HSV.

It is an additional object to provide compounds useful in the preparation of ion exchange resins or chiral media.

It is a further object to provide intermediates and methods for making such compounds.

These and other objects will be more fully understood by further reference to the disclosures herein.

SUMMARY OF THE INVENTION

In accordance with the invention, novel compounds are provided having formula (I)

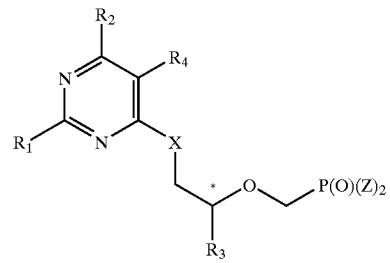

(I)

where $R_1$ is H, amino or methylsulfanyl;

$R_2$ is H, methyl, halo, —$N(R_5)_2$, hydroxy, protected hydroxy or a group of the formula (Ia)

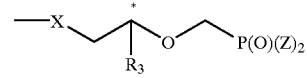

(Ia)

$R_3$ is independently H, methyl, hydroxymethyl, halomethyl or protected hydroxymethyl;

$R_4$ is H or halo;

X independently is oxygen, sulfur or a bond;

Z independently is hydroxy, an ester or amide;

$R_5$ is independently H, $C_1$–$C_8$ alkyl or a protecting group; and

* designates a chiral carbon atom; and salts and solvates thereof.

The objects also are accomplished by a method for preparation of compounds of the formula (I)

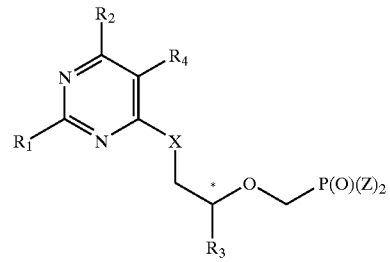

(I)

where $R_1$, $R_2$, $R_3$, $R_4$, X, Z, $R_5$ and * are defined above;

comprising reacting a compound of formula (II)

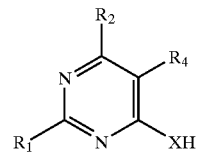

(II)

where $R_1$ and $R_5$ are defined above;

$R_2$ is H, methyl, halo, —$N(R_5)_2$, hydroxy or protected hydroxy; and

X is O or S;

with a compound of the formula (III)

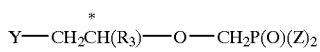

where
- Z is an ester or an amide;
- * designates a chiral carbon atom;
- $R_3$ is H, methyl, halomethyl or protected hydroxymethyl; and
- Y is a leaving group in dipolar aprotic solvent in the presence of a base to obtain a compound of formula (I) where Z is ester or amide; (b) one or both Z groups optionally are converted to produce the compound of formula (I) where at least one Z is hydroxy.

In another embodiment of this invention, a method is provided for the preparation of compounds of formula (I) where
- $R_1$ is H, amino or methylsulfanyl;
- $R_2$ is $-N(R_5)_2$
- $R_3$ is independently H, methyl, hydroxymethyl, halomethyl or protected hydroxymethyl;
- $R_4$ is H or halo
- X is oxygen or sulfur;
- Z independently is hydroxy, an ester or amide;
- $R_5$ is independently H, $C_1$–$C_8$ alkyl or a protecting group; and
- * designates a chiral carbon atom comprising reacting a compound (IV)

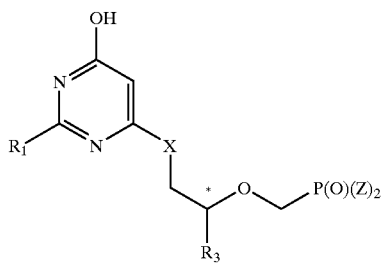

where
- $R_3$ is H, methyl, halomethyl or protected hydroxymethyl;
- X is O or S; and
- Z is amide or ester;

with $N(R_5)_2$. One or both Z groups optionally are converted to the compound of formula (I) where at least one Z is hydroxy.

In another embodiment, a method is provided for preparation of compounds of formula (V)

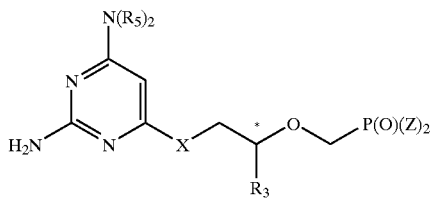

where
- $R_3$ is H, methyl, hydroxymethyl, halomethyl or protected hydroxymethyl;

- $R_5$ independently is H, $C_1$–$C_8$ alkyl or a protecting group;
- X is oxygen or sulfur;
- Z independently is hydroxy, an ester or amide; and
- * designates a chiral carbon atom;

comprising reacting compound (IVa)

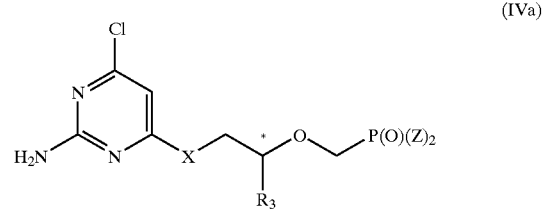

with $N(R_5)_2$ in anhydrous solvent, alkali hydroxide or alkali carbonate in aqueous solution and Z is optionally converted to the compound of formula (V) wherein 1 or 2 Z groups are hydroxy.

In another embodiment, a method is provided for the preparation of compounds of formula (VI)

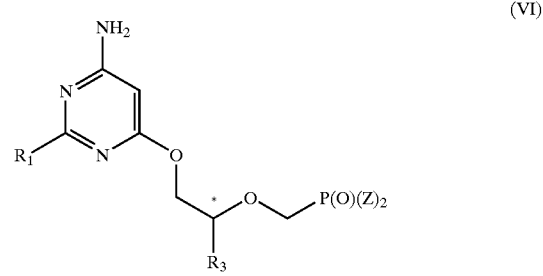

where
- $R_1$ is H, amino or methylsulfanyl;
- $R_3$ is H, methyl, hydroxymethyl, halomethyl or protected hydroxymethyl;
- Z independently is hydroxy, an ester or amide; and
- * designates a chiral carbon atom;

comprising reacting a compound of formula (VII)

where
- $R_1$ is H, amino or methylsulfanyl with a compound of the formula (VIII)

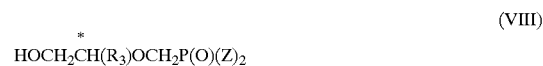

where Z is amide or ester in the presence of a base. Optionally one or both Z groups are converted to produce a hydroxy.

In another embodiment of this invention, a method is provided for the preparation of compounds of formula (XIII)

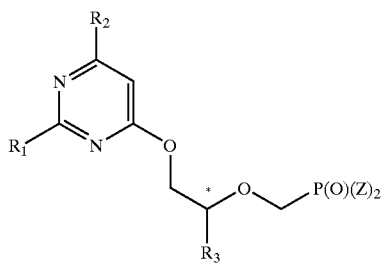
(XIII)

where
R₁ is H, amino or methylsulfanyl;
* is a chiral carbon atom;
R₂ is H, chloro, hydroxy or amino;
R₃ is H, methyl, halomethyl or hydroxymethyl; and
Z is amide or ester;
comprising (a) reacting a compound of the formula (IX)

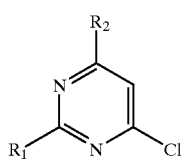
(IX)

where
R₁ is H, amino or methylsulfanyl;
R₂ is H, chloro or amino;
with a compound of the formula (X)

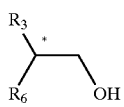
(X)

where
R₃ is H, methyl, hydroxymethyl, halomethyl or protected hydroxymethyl;
* is a chiral carbon atom;
R₆ is hydroxy or protected hydroxy;
or R₃ and R₆ are joined by a cyclic acetal or ketal protecting group;
in the presence of a base without solvent or in the presence of an aprotic solvent to produce a compound of formula (XI)

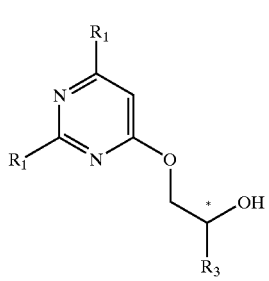
(XI)

where
R₁ is H, amino or methylsulfanyl;
* is a chiral carbon atom;

R₂ is H, chloro or amino; and
R₃ is H, methyl, halomethyl or protected hydroxymethyl; and
(b) reacting compound (XI) with a compound of the formula (XII)

Y—CH₂P(O)(OZ)₂ (XII)

where
Y is a leaving group;
Z is amide or ester in the presence of a base in dimethylformamide or tetrahydrofurane to produce a compound of formula (XIII); and
(c) optionally hydrolyzing Z group in compound (XIII) to produce a compound of formula (VI) where 1 or 2 Z groups are hydroxy and X is oxygen atom.

In another embodiment of this invention, a method is provided for the preparation of compounds of formula (I) where
R₁ is H, amino or methylsulfanyl;
R₃ is H, methyl, hydroxymethyl, halomethyl or protected hydroxymethyl;
R₄ is halo;
X is oxygen;
Z independently is hydroxy, an ester or amide; and
* designates a chiral carbom atom;
comprising (a) reacting a compound of the formula (VI) where
R₁ is H, amino or methylsulfanyl;
R₃ is H, methyl, hydroxymethyl, halomethyl or protected hydroxymethyl;
Z independently is an ester; and
* designates a chiral carbon atom;
with elemental halogen in an inert solvent to produce a compound of formula (I).

Optionally one or both Z groups are converted to hydroxy.

Further objects of this invention are accomplished by a method comprising administering a therapeutically effective amount of a compound of formula (I) to a patient in need of such treatment.

DETAILED DESCRIPTION OF THE INVENTION

As used herein, and unless modified by the immediate context, alkyl means branched, normal or cyclic saturated hydrocarbons and includes methyl, ethyl, propyl, cyclopropyl, cyclobutyl, isopropyl, n-, sec-, iso- and tert-butyl, pentyl, isopentyl, 1-methylbutyl, 1-ethylpropyl, neopentyl, and t-pentyl.

Halo typically means chloro, but includes bromo, fluoro, or iodo.

R₁ typically is H or amino, but also can be methylsulfanyl (i.e. methylthio).

R₂ generally is hydroxy or —N(R₅)₂ where R₅ independently is H or C₁–C₈ alkyl.

R₃ typically is H or methyl, but may be hydroxymethyl (typically (S) configuration substantially free of the (R) enantiomer) or halomethyl, and, if methyl or halomethyl, preferably is in the (2R) configuration substantially free of the (2S) configuration. Halomethyl generally is fluoromethyl.

R₅ generally is H, but also can be lower (C₁–C₃) alkyl (one or both instances).

As is further described infra, Z is suitably any ester or amide heretofore known for use with nucleotide phosphonates. When Z is an ester, it has the structure $OR_7$. $R_7$ ordinarily is H (i.e., Z is hydroxy) in compounds having antiviral activity per se, although other $R_7$ ester groups described below are suitable for use as protecting groups or as pro-functionalities for prodrug embodiments.

X preferably is O.

Z is an ester or amide when it is desired to protect the compounds of this invention against undesired reactions or when the object is to provide an in vivo prodrug of the compound. Otherwise, Z is OH.

The esters or amides are useful as protected intermediates in the synthesis of compounds of this invention where Z=OH. In this embodiment, the selection of ester or amide may not be important, depending upon the nature of the reaction involved. All that is needed is that the Z substituent not be removed until the step in synthesis at which this is desired, and if this is not apparent on theoretical grounds it can be readily determined by rudimentary experiments. For example, esters in particular are used to protect the phosphonate hydroxy groups against alkylation.

When Z serves as a prodrug functionality, the ester or amide is removed in vivo from the phosphonate. Suitable prodrug esters or amidates optionally are selected based on the substrate specificity of esterases and/or carboxypeptidases expected to be found within cells where precursor hydrolysis is desired. To the extent that the specificity of these enzymes is unknown, one will screen a plurality of nucleotide analogues of this invention until the desired substrate specificity is found. This will be apparent from the appearance of free phosphonate or antiviral activity. One generally selects compounds that are (i) not hydrolyzed or hydrolyzed comparatively slowly in the upper gut, (ii) gut and cell permeable and (iii) are hydrolyzed in the cell cytoplasm and/or systemic circulation. Screens with cells from particular tissues are used to identify precursors that are released in organs susceptible to a target viral or microbial infection, e.g. in the case of liver, precursor drugs capable of hydrolysis in the liver. Other infections, e.g. CMV or HIV, optionally are treated with a precursor that is hydrolyzed at substantially the same rate and to substantially the same degree in all tissues. Assays known in the art are suitable for these purposes, including intestinal lumen stability, cell permeation, liver homogenate stability and plasma stability assays. These assays are used to determine the bioavailability characteristics of the precursors.

Typical examples of ester and amide substituents group Z are found in WO95/07920, WO98/04569 and EP 481214 A1. Any ester or amide genus or species described in these publications (and in the preference order set forth in such publications) can be used as group Z herein.

Usually, both Z are hydroxyl or both are ester and/or amide, i.e, typically 2 or no Z groups are hydroxy. In general, when neither Z is OH then one Z is amide and one is ester. Amides with naturally occurring amino acids and a esters with phenyl are preferred. The free carboxyl(s) of amino acid Z groups generally are esterified with $C_1$-$C_8$ alkyl.

In general, Z is hydroxy in compounds to be used directly for antiviral purposes, i.e. such compounds are employed without any requirement for hydrolysis in vivo of the ester or amide.

Protecting groups for hydroxyl include acetals, ketals or $C_1$-$C_8$ alkyl. A typical protecting group for amino is trityl. Other conventional protecting groups are known (Greene et al., "Protecting Groups in Organic Synthesis, $2^{nd}$ Ed. 1991, pp. 10–142 and 309–405).

Utilities

The compounds of the invention are useful for the treatment of viruses, or as intermediates in the preparation of such compounds. Exemplary viral infections to be treated or to be tested for susceptibility to compounds of this invention include infections caused by DNA or RNA viruses such as herpesviruses (CMV, HSV 1, HSV 2, EBV, varicella zoster virus [VZV], bovid herpesvirus type 1, equid herpesvirus type 1, HHV-6, papillomaviruses (HPV types 1–55 including carcinogenic HPV), flaviviruses (including yellow fever virus, African swine fever virus and Japanese encephalitis virus), togaviruses (including Venezuelan equine encephalomyelitis virus), influenza viruses (types A–C), retroviruses (HIV-1, HIV-2, HTLV-I, HTLV-II, SIV, FeLV, FIV, MoMSV), adenoviruses (types 1–8), poxviruses (vaccinia virus), enteroviruses (poliovirus types 1–3, Coxsackie, hepatitis A virus, and ECHO virus), gastroenteritis viruses (Norwalk viruses, rotaviruses), hantaviruses (Hantaan virus), polyomavirus, papovaviruses, rhinoviruses, parainfluenza virus types 1–4, rabies virus, respiratory synctial virus (RSV), hepatitis viruses A, B, C and E, and the like.

Preferred compounds of this invention for the treatment of herpes viruses, hepadna viruses and HIV are those in which $R_1$=$NH_2$, $R_2$=$NH_2$ or OH, X=O and $R_3$=H or methyl. Other antiviral activities of compounds of this invention are determined by routine assay of antiviral activity using enzyme inhibition assays, tissue culture assays, animal model assays and the like as will be understood by those skilled in the art.

The novel compounds of this invention also are useful per se or as intermediates in the preparation of polymers having a wide variety of diagnostic, therapeutic and industrial utilities.

The compounds of this invention are suitable as intermediates to prepare affinity absorption media bearing substituent groups having properties useful for absorbing compounds from impure mixtures. These are prepared and used in the same fashion as other ion exchange media containing the same substituents, e.g. phosphonate or amino. For example, the phosphonate group of the compounds herein are covalently bound to insoluble matrix and free $R_1$ amino substituents on the heterocyclic base serve as ion exchange sites. Alternatively, the heterocyclic base amino group is linked to the matrix and the free phosphonate group is then useful in the chromatographic absorption of positively charged molecules. Other immobilized embodiments of the compounds herein are useful in purifying proteins, e.g., enzymes to which the compounds of this invention may bind, e.g. transport proteins (see Cihlar, supra).

Suitable methods of incorporation of the compounds of this invention into insoluble matrices such as polymeric resins will be readily apparent to the skilled artisan. The compounds herein can be immobilized by covalently crosslinking the pyrimidine amino or hydroxy groups to an insoluble matrix. Similarly, compounds of this invention are incorporated into insoluble resins by binding the hydroxy of the phosphonate group or a hydroxymethyl $R_3$ group to the matrix or resin using covalent linking agents heretofore known. Suitable linking methods are described in Cihlar (supra).

The compounds of this invention also are useful as cross-linkers or spacers in preparing affinity absorption matrices (as opposed to functioning as affinity moieties per se as noted in the preceding paragraphs). The compounds herein contain a multiplicity of functional groups that are suitable as sites for cross-linking desired substances. It is conventional to link affinity reagents such as hormones, peptides, antibodies, enzymes, drugs, and the like to insoluble substrates. These insolubilized reagents are employed in known fashion to absorb substances from manufactured preparations, diagnostic samples and other impure mixtures. Similarly, immobilized enzymes are used to perform catalytic conversions with facile separation of enzyme from product.

In some embodiments, it is not necessary that the compounds of this invention be cross-linked to insoluble materials. For example, they can be used to link analytes to detectable groups in preparing soluble diagnostic reagents.

Methods for cross-linking using the substituent groups found in the compounds of this invention are well known in the art. For example, the phosphonic acid is used to form esters with alcohols or amides with amines. Similarly, the amino, halo, hydroxy and other reactive sites found on the pyrimidine are suitable. Of course, protection of reactive groups will be used where necessary while assembling the cross-linked reagent. In general, the inventive compounds are used by linking them through phosphonic acid to the hydroxy or amino groups of the linking partner, and covalently bonded to the other binding partner through another substituent of the compound of this invention. For example a first binding partner such as a steroid hormone is esterified to the phosphonic acid of this invention and then this conjugate is cross-linked through $R_3$ hydroxymethyl to cyanogen bromide activated Sepharose, whereby the immobilized steroid is obtained. Other chemistries for conjugation are well known. See, for example Maggio, "Enzyme-Immunoassay" (CRC, 1988, pp 71–135) and references cited therein.

Pharmaceutical Formulations

The compounds of this invention and their physiologically acceptable salts and solvates (hereafter collectively referred to as the active ingredients) are formulated for administration by any route appropriate to the condition to be treated. The compounds and formulations preferably will be sterile.

The active ingredients are placed into pharmaceutical formulations. The formulations, both for veterinary and for human use, comprise at least one active ingredient, as above defined, together with one or more acceptable carriers therefor and optionally other therapeutic ingredients. The carrier(s) must be "acceptable" in the sense of being compatible with the other ingredients of the formulation and not deleterious to the recipient.

The formulations conveniently are presented in unit dosage form and may be prepared by any of the methods well known in the art of pharmacy. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

For external infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), typically 0.2 to 15% w/w and most typically 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxy groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogues.

The oily phase of the emulsions of this invention may be constituted from known ingredients in a known manner. This phase may comprise an emulsifier alone, or a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate. Suitable oils or fats include straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate or 2-ethylhexyl palmitate. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is typically is present in such formulations in a concentration of 0.01 to 20% by weight.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered by rapid inhalation through the nasal passage from a container of the powder. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of pneumocystis pneumonia.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

The present invention further provides veterinary compositions comprising at least one active ingredient as above defined together with a veterinary carrier therefor. Veterinary carriers are materials for administering the composition and may be solid, liquid or gaseous materials which are otherwise inert or acceptable in the veterinary art and are compatible with the active ingredient. These veterinary compositions may be administered orally, parenterally or by any other desired route.

Compounds herein optionally are used in controlled release pharmaceutical formulations containing as active ingredient one or more active compounds in which the release of the active ingredient is controlled and regulated to allow less frequent dosing or to improve the pharmacokinetic or toxicity profile of a given compound. In general, the compounds are administered from controlled release systems such as the implant of WO 92/14450 or U.S. Pat. No. 5,098,443, or the matrices of U.S. Pat. No. 4,740,365 or U.S. Pat. No. 5,141,752. Many others are known and are suitable for use herein.

Therapeutic Administration

Suitable routes for administration include oral, rectal, nasal, topical (including ocular, buccal and sublingual), vaginal and parenteral (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

For each of the above-indicated therapeutic indications the amount required of an active ingredient (as above defined) will depend upon a number of factors including the severity of the condition to be treated, the infectious agent, whether the use is prophylactic or to treat an acute infection, the site of infection or pathology and other factors ultimately at the discretion of the attending physician or veterinarian. In general, however, a suitable dose for consideration by the clinician will be in the range of analogous methoxyphosphonates (see supra), taking into account differences in potency in in vitro testing, generally 0.1 to 250 mg per kilogram bodyweight of recipient per dose (including active ingredient(s) in a range between 0.1 mg and 400 mg/Kg/dose in increments of 0.5 mg/Kg/dose such as 2.5 mg/Kg/dose, 3.0 mg/Kg/dose, 3.5 mg/Kg/dose, etc), typically in the range 0.5 to 50 mg per kilogram body weight per dose and most usually in the range 1 to 300 mg per kilogram body weight per dose.

The desired dose is administered at appropriate intervals in unit dosage forms, usually with a relatively higher induction dose and lower, less frequent maintenance doses. The compounds also are used prophylactically, for example, by administration on about from 1 to 7 days before viral infection. HPV tumors or growths and herpes lesions often are treated topically, either by local injection or by topical gels, ointments or the like.

The compounds of the invention optionally are employed in combination with other therapeutic agents for the treatment or prophylaxis of the infections or conditions indicated above. Examples of such further therapeutic agents include agents that are effective for the treatment or prophylaxis of viral infections. These include but are not limited to the NRTIs, 3'-azido-3'-deoxythymidine (zidovudine, AZT), 2'-deoxy-3'-thiacytidine (3TC), 2',3'-dideoxy-2',3'-didehydrothymidine (D4T), carbovir (carbocyclic 2',3'-dideoxy-2',3'-didehydroguanosine), abacavir (ABC), 2',3'-dideoxyinosine (D4T), didanosine, 2',3'-dideoxycytidine (ddc, zalcitabine), 3'-azido-2',3'-dideoxyuridine, (E)-5-(2-bromovinyl)-2'-deoxyuridine (BVDU), 2-chloro-2'-deoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-β-D-arabinosyl)-5-iodocytidine (FIAC), tetrahydroimidazo(4,5,1-jk)-(1,4)-benzodiazepin-2(1H)-thione (TIBO) or other non-nucleoside reverse transcriptase inhibitors (e.g. nevirapine, delaviridine, efavirens, daparivine, etc.), protease inhibitors (e.g. saquinavir, indinavir, ritonovir, amprenavir, and the like), 2'-norcyclicGMP, 6-methoxypurine arabinoside (ara-M), 6-methoxypurine arabinoside 2'-O-valerate, cytosine arabinoside (ara-C), acyclic nucleosides such as acyclovir, valacyclovir, penciclovir, famciclovir, ganciclovir, acyclic nucleotide analogues such as HPMPC, PMEA, PMEG, PMPA, PMPDAP, FPMPA, HPMPA and HPMPDAP, (2R, 5R)-9-[tetrahydro-5-(phosphonomethoxy)-2-furanyl] adenine, (2R, 5R)-1-[tetrahydro-5-(phosphonomethoxy)-2-furanyl]thymine, other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodium phosphonoformate.

Synthesis Methods

Compounds falling within the formula (I) are synthesized by alkylating the corresponding 6-hydroxypyrimidine base with dialkyl 2-chloroethoxymethylphosphonate (or its analogues yielding other $R_3$ groups) in the presence of NaH, $Cs_2CO_3$ or DBU (1,8-diazabicyclo[5.4.0]undec-7-ene) in dipolar aprotic solvent, usually DMF, optionally followed by deprotection, e.g. with bromotrimethylsilane and subsequent hydrolysis. The product of the formula (I) is accompanied by formation of varying amounts of the corresponding N1-isomer, i.e. 2,4-disubstituted 1-[2-(phosphonomethoxy) ethyl]pyrimidin-6-one. It can be removed by chromatography as the neutral diester prior to the bromotrimethylsilane treatment.

Another method of preparation of compounds of the formula (I) comprises the transformation of 2-substituted 4-chloro-6-[2-(phosphonomethoxy)ethoxy]pyrimidine derivatives (and its $R_3$ analogues) by reaction with primary or secondary amines in anhydrous solvents (e.g. ethanol), alkali hydroxide or alkali carbonate in water. This reaction can be catalyzed e.g. by 1,3,5-triazole, imidazole, or, to an advantage, with DABCO (diazabicyclooctane). The protecting groups optionally are then removed, e.g. by bromotrimethylsilane treatment and hydrolysis.

Compounds of formula (I) can be also obtained by the reaction of 2,4-disubstituted 6-halogenopyrimidines with sodium alkoxide of dialkyl 2-hydroxyethylphosphonate (or its analogues yielding other $R_3$ groups) followed by optional deprotection. The advantage of this procedure consists in the formation of the required O6-isomer only. The selection of the suitable synthetic procedure depends on the availability of the heterocyclic pyrimidine derivative used as a starting material.

Compounds of formula (I) can be also obtained by the reaction of 2,4-disubstituted 6-(2-hydroxyalkyl)pyrimidines with dialkyl p-toluenesulfonyloxymethylphosphonate in the presence of NaH. The starting materials are prepared by treatment of the appropriate 6-chloropyrimidine with a protected or unprotected diol in the presence of a base.

Compounds of formula (I) can be further obtained by substitution at diverse positions of the pyrimidine ring. Thus, the 5-halo derivatives can be obtained by reactions with elemental halogen or by halogen anion exchange reactions.

Z group amides or esters are converted to hydroxyl by hydrolysis.

Monoesters are easily available from the diester or a mixture of di- and monoesters by treatment with lithium or sodium azide in DMF (A. Holy, "Synthesis 1998" 381–385 (1998)).

All citations are expressly incorporated by reference.

The invention will be more fully understood by reference to the following examples.

EXAMPLE 1

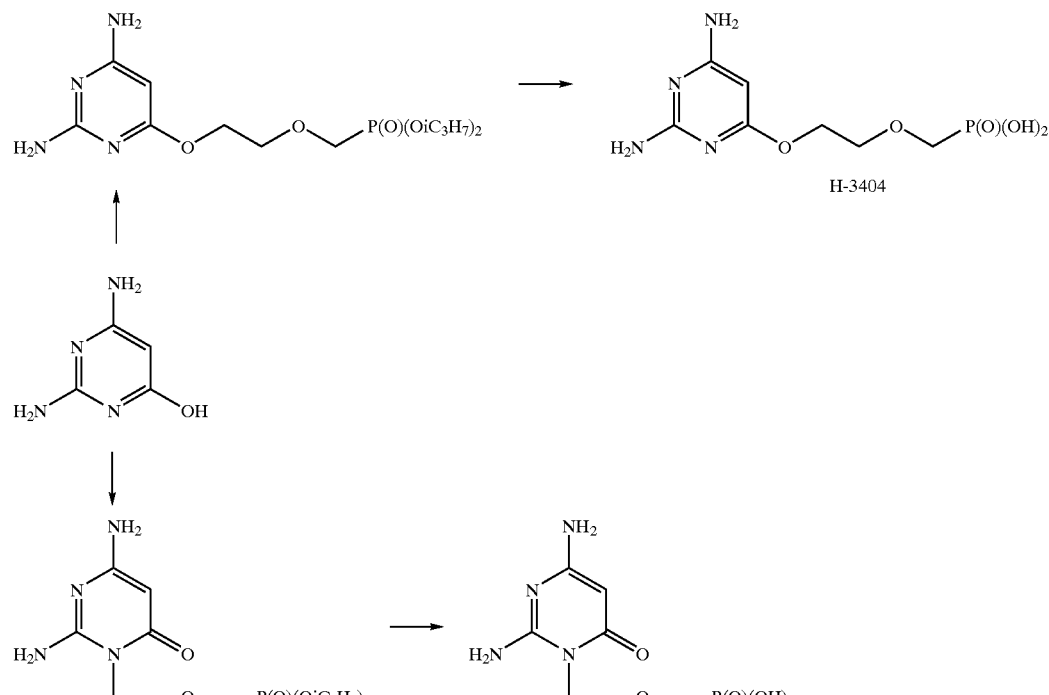

(a) 2,4-Diamino-6-[2-(phosphonomethoxy)ethoxy]pyrimidine and 2,4-Diamino-1-[2-(phosphonomethoxy)ethyl]pyrimidine-6(1H)-one A mixture of 2,4-diamino-6-hydroxypyrimidine (2.52 g, 20 mmol), cesium carbonate (3.25 g, 10 mmol) in dimethylformamide (40 mL) was stirred 30 min at 80° C. and diisopropyl 2-chloroethoxymethylphosphonate (3.5 mL, 23.4 mmol) was added. The mixture was stirred 16 h at 100° C. and filtered from salts. The filtrate was taken down in vacuo and the residue chromatographed on silica gel column (300 mL) with chloroform. The elution gave product which was crystallized from ethyl acetate—petroleum ether to afford 1.2 g (17.2%) of 2,4-diamino-6-[2-(diisopropylphosphonylmethoxy)ethoxy]pyrimidine, m.p. 159° C. For $C_{13}H_{25}N_4O_5P$ (348.3) calculated 44.83% C, 7.23% H, 16.08% N, 8.89% P; found 44.99% C, 7.28% H, 16.18% N, 9.03% P. Mass spectrum: 349.3 (MH$^+$)(100), 265.1 (MH$^+$–2×iPr)(6); 139 (26); 127.1 (BaseH$^+$)(37). $^1$H NMR (CD$_3$SOCD$_3$): 1.24 d, 6H and 1.24 d, 6H, J(CH$_3$, CH)=6.2 (4×CH$_3$); 3.74 m, 2H (H-2'); 3.78 d, J(CH$_2$—P)=8.2 (CH$_2$—P); 4.22 m, 2H (H-1'); 4.59 dh, 2H, J(CH,P)=8.2, J(CH,CH$_3$)=6.2 (2×CH); 5.02 s, 1H (H-6); 5.85 bs, 2H and 6.00 bs, 2H (2×NH$_2$). $^{13}$C NMR (CD$_3$SOCD$_3$): 23.85 d, J(CH$_3$,P)=4.6 (2×CH$_3$); 23.99 d, J(CH$_3$,P)=4.1 (2×CH$_3$); 63.65 (C-1'); 65.02 d, J(CH$_2$—P)=164.4 (CH$_2$P); 70.32 d, J(CH,P)=6.0 (2×CH—O); 71.05 d, J(2',P)=11.9 (C-2'); 76.35 (C-5); 163.01, 166.15 and 169.92 (C-2, C-4 and C-6).

This compound (1.0 g, 2.9 mmol) was treated with BrSiMe$_3$ (4 mL) in acetonitrile (40 mL) overnight. The solvents were stripped down in vacuo, the residue codistilled with acetonitrile (2×25 mL) and water (50 mL) was added to the residue. The solution was alkalized with conc. aqueous ammonia and evaporated in vacuo. The residue was applied in aqueous solution onto a column (100 mL) Dowex 50×8 (H$^+$-form) and the column was eluted with water (3 mL/min); the elution was followed by continuous measurement of UV-absorption of the eluate at 254 nm. After removal of the neutral UV-absorbing fraction the column was eluted with 2.5% aqueous ammonia and the UV-absorbing fraction was collected. It was taken down in vacuo, redissolved in water (20 mL), brought to pH 9–10 by conc. aqueous ammonia and applied on a column (70 mL) Dowex 1×2 (acetate form) thoroughly prewashed with water. Elution with water gave (with retention) product which was crystallized from water to afford 2,4-diamino-6-[2-(phosphonomethoxy)ethoxy]pyrimidine (0.60 g, 78.3%), m.p. 279° C. (water). E$_{Up}$ 0.80. For $C_7H_{13}N_4O_5P$ (264.2)

calculated 31.83% C, 4.96% H, 21.21% N, 11.72% P; found 31.52% C, 5.04% H, 20.96% N, 11.53% P. UV-spectrum [$\lambda_{max}(\epsilon_{max})$] (pH 2): 276 (9100), (pH 7): 265 (7500). These data agree with the UV-spectra published for 2,4-diamino-6-methoxypyrimidine (($\lambda_{max}$263 and 275, resp.). $^1$H NMR (CD$_3$SOCD$_3$, 40° C.): 3.58 d, 2H, J(CH$_2$,P)=8.7 (CH$_2$P); 3.74 t, 2H, J(2',1')=4.9 (H-2'); 4.23 t, 2H, J(1',2')=4.9 (H-1'); 5.07 s, 1H (H-5); 5.86 bs, 2H and 6.01 bs, 2H (2×H$_2$). $^1$H NMR (D$_2$O): 3.69 d, 2H, J(CH$_2$,P)=8.7 (CH$_2$P); 3.91 m, 2H (H-2'); 4.30 m, 2H (H-1'); 5.45 s, 1H (H-5). $^{13}$C NMR (D$_2$O): 69.30 (C-1'); 70.28 d, J(CH$_2$—P)=151.3 (CH$_2$P); 73.35 d, J(2',P)=10.3 (C-2'); 79.63 (C-5); 165.46, 169.35 and 171.08 (C-2, C-4 and C-6). Lowfield position of C-1'-carbon signal in the O-isomers (diester and free phosphonate) ($\delta$ 63.65 and 69.30, respectively) indicates that the PME-group is linked to the oxygen atom at C-6.

Further elution of the silica gel column with chloroform gave 1.8 g (26%) of amorphous 2,4-diamino-1-[2-(diisopropylphosphonylmethoxy)ethyl]pyrimidine-6(1H)-one (R$_F$0.35, S1) which was dried in vacuo over P$_2$O$_5$. M.p. 196–197° C. The residue (5.17 mmol) was treated with bromotrimethylsilane (6 mL) in acetonitrile (60 mL) overnight and worked up as described for the O-isomer. Purification of the desalted mixture on Dowex 1 column (elution with water) gave product which was crystallized from water to afford 0.95 g (65%) of 2,4-diamino-1-[2-(phosphonomethoxy)ethyl]pyrimidine-(1H)-one, m.p. 228° C. (water). E$_{Up}$ 0.90. For C$_7$H$_{13}$N$_4$O$_5$P.H$_2$O (282.2) calculated 29.79% C, 5.36% H, 19.85% N, 10.98% P; found 29.76% C, 5.22% H, 20.01% N, 10.92% P. Mass spectrum: 349.2 (MH$^+$)(100); 265.1(MH$^+$-2×iPr)(35); 126 (BH$^+$) (26). UV-spectrum [$\lambda_{max}(\epsilon_{max})$] (pH 2): 264 (18000), (pH 7): 267 (12200). The $\lambda_{max}$ value coincides with the value published for 2,4-diamino-1-methylpyrimidine-6(1H)-one (268 nm). $^1$H NMR (CD$_3$SOCD$_3$): 3.59 d, 2H, J(CH$_2$,P)=8.4 (CH$_2$P); 3.60 t, 2H, J(2',1')=6.1 (H-2'); 3.96 t, 2H, J(1',2')=6.1 (H-1'); 4.61 s, 1H (H-5); 5.88 bs, 2H and 6.61 bs, 2H (2×NH$_2$).$^1$H NMR (D$_2$O): 3.48 D, 2H, J(CH$_2$,P)=8.4 (CH$_2$P); 3.76 t, 2H, J(1',2')=5.2 (H-1'); 4.09 t, 2H, J(2',1')=5.2 (H-2'); 5.06 s, 1H (H-5). $^{13}$C NMR (D$_2$O): 45.15 (C-1'); 70.41 d, J(CH$_2$—P)= 154.7 (CH$_2$P); 74.09 d, J(2',P)=11.8 (C-2'); 81.05 (C-5); 159.73, 166.79 and 168.04 (C-2, C-4 and C-6). The upfield position of C-1' ($\delta$ 45.15) indicates N-substitution. Two signals of NH$_2$ groups ($\delta$ 6.61 and 5.88) which are observed in $^1$H NMR spectrum in DMSO exclude the substitution at the exo-positions 2-NH$_2$ and/or 4-NH$_2$ and are consistent with the expected substitution at N(1).

EXAMPLE 2

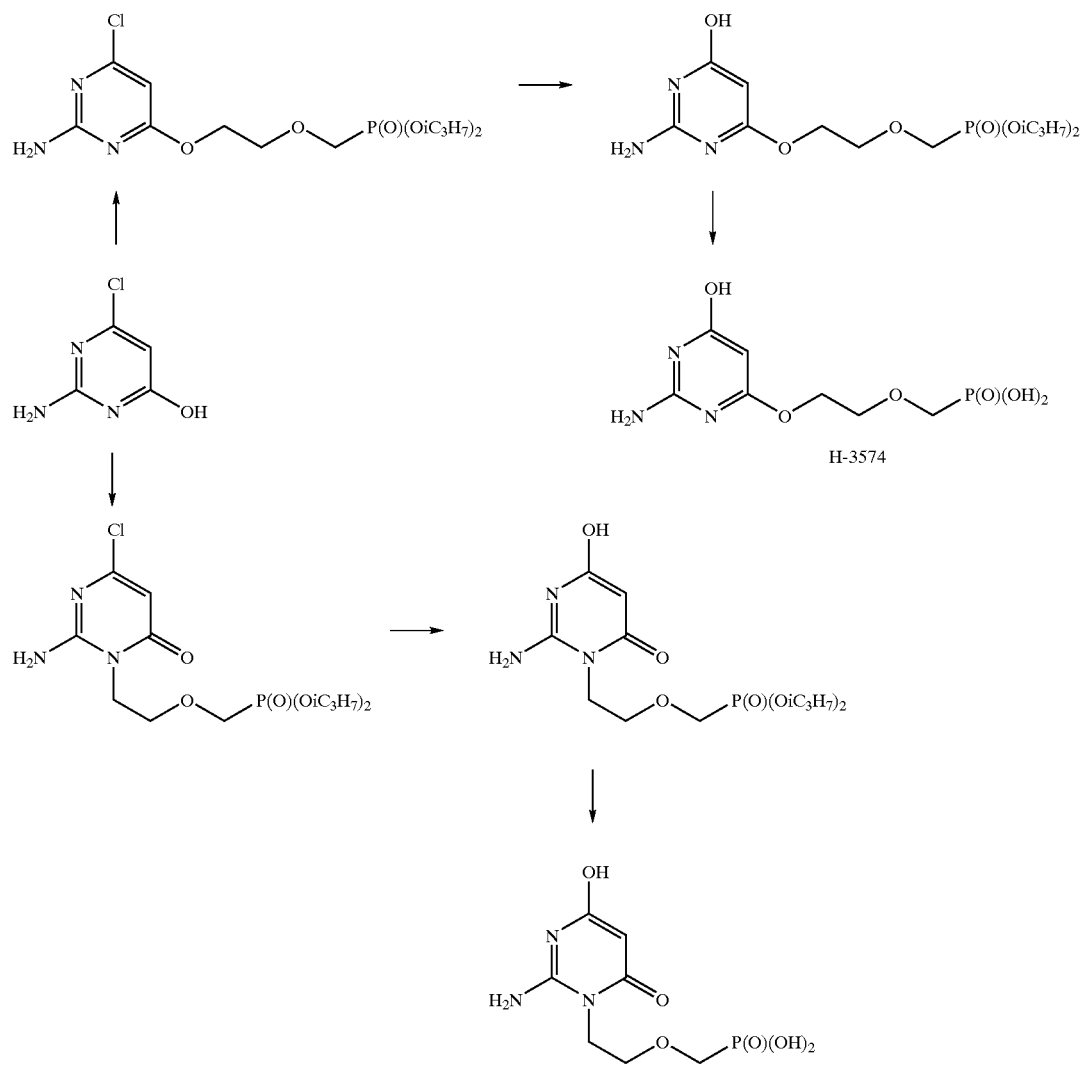

(a) 2-Amino-4-chloro-6-[2-(diisopropylphosphonylmethoxy)ethoxy]pyrimidine and 2-amino-4-chloro-1-[2-(diisopropylphosphonylmethoxy)ethyl]pyrimidin-6(1H)-one 2-Amino-4-chloro-6-hydroxypyrimidine monohydrate (25 mmol) was codistilled with toluene (3×50 mL) in vacuo, and the residue was treated with DMF (50 mL), DBU (3.8 mL) and diisopropyl 2-chloroethoxymethylphosphonate (7 mL). The mixture was stirred 16 h at 100° C. and the volatiles removed by evaporation at 50° C./2 kPa. The residue was taken in chloroform (200 mL), filtered and washed with saturated NaCl (100 mL). The aqueous wash was extracted with chloroform (5×50 mL), the combined extracts were dried with magnesium sulfate and evaporated. Separation on silica gel column (150 mL) in chloroform by chloroform-ethanol gradient gave 2-amino-4-chloro-6-[2-(diisopropylphosphonyl-methoxy)ethoxy]pyrimidine, yield 27.2%, m.p. 89° C. For $C_{13}H_{23}ClN_3O_5P$ (367.77) calculated 42.46% C, 6.30% H, 9.64% Cl, 11.43% N, 8.42% P; found 42.34% C, 6.34% H, 9.79% Cl, 11.30% N, 8.23% P. Mass-spectrum: 368.3 (MH$^+$)(100).$^1$H NMR (CD$_3$SOCD$_3$): 1.22 d, 6H and 1.23 d, 6H, J(CH$_3$,CH)=6.1 (CH$_3$); 3.78 d, J(CH$_2$—P)=8.3 (CH$_2$—P); 3.80 m, 2H (H-2'); 4.37 m, 2H (H-1'); 4.58 m, 2H (P—OCH); 6.06 s, 1H (H-5); 7.05 bs, 2H (NH$_2$). $^{13}$C NMR (CD$_3$SOCD$_3$): 23.83 d, 2C, J and 23.97 d, 2C, J(P,C)=3.9 (CH$_3$); 65.00 d, J(P,C)=164.1 (P—C); 65.15 (C-1'); 70.35 d, 2C, J(P,C)=6.7 (P—OC); 70.52 d, 2C, J(P,C)=11.7 (C-2'); 94.46 (C-5); 160.12 (C-2); 162.97 (C-4); 170.56 (C-6).

Further elution and crystallisation from ethyl acetate-ether gave 2-amino-4-chloro-1-[2-(diisopropylphosphonylmethoxy)ethyl]pyrimidin-6(1H)-one, yield 52.4%, m.p.95° C. For $C_{13}H_{23}ClN_3O_5P$ (367.77) calculated 42.46% C, 6.30% H, 9.64% Cl, 11.43% N, 8.42% P; found 42.28% C, 6.22% H, 9.65% Cl, 11.50% N, 8.27% P. Mass-spectrum: 368.4 (MH$^+$)(100). $^1$H NMR (CD$_3$SOCD$_3$): 1.20 d, 6H and 1.22 d, 6H, J(CH$_3$,CH)=6.1 (CH$_3$); 3.69 t, 2H, J(2',1')=5.5 (H-2'); 3.76 d, J(CH$_2$—P)=8.1 (CH$_2$—P); 4.06 t, 2H, J(1',2')=5.5 (H-1'); 4.55 m, 2H (P—OCH); 5.67 s, 1H (H-5); 7.60 bs, 2H (NH$_2$). $^{13}$C NMR (CD$_3$SOCD$_3$): 23.84 d, 2C, J(CH$_3$,P)=3.9 and 23.97 d, 2C, J(P,C)=3.9 (CH$_3$); 40.29 (C-1'); 65.03 d, J(P,C)=164.1 (P—C); 69.01 d, 2C, J(P,C)=11.7 (C-2'); 70.41 d, 2C, J(P,C)=5.9 (P—OC); 98.28 (C-5); 155.73 (C-2); 157.87 (C-4); 161.48 (C-6).

(b) 2-Amino-4-hydroxy-6-[2(phosphonomethoxy)ethoxy]pyrimidine

A mixture of 2-amino-4-chloro-6-[2-(diisopropylphosphonylmethoxy)ethoxy]pyrimidine (5.7 g), DABCO (3.6 g) and K$_2$CO$_3$ (9.0 g) in water (100 mL) was refluxed 150 min under stirring, cooled and acidified by addition of Dowex 50×8 (H$^+$-form). The suspension was alkalified with conc. aqueous ammonia and, after 5 min stirring, filtered and the resin washed with 50% aqueous methanol (200 mL). The filtrate was evaporated to dryness, ethanol (50 mL) was added and the mixture evaporated to dryness. The residue gave on chromatography on silica gel column (150 mL) with chloroform-ethanol gradient crystalline 2-amino-6-[2-(diisopropylphosphonylmethoxy)ethoxy]-4-hydroxypyrimidine, m.p.154° C. in 78% yield. For $C_{13}H_{24}N_3O_6P$ (349.3) calculated 44.70% C, 6.92% H, 12.03% N, 8.37% P; found 44.58% C, 7.02% H, 11.95% N, 8.53% P. $^1$H NMR (CD$_3$SOCD$_3$): 1.24 d, 6H and 1.23 d, 6H, J(CH$_3$,CH)=6.2 (4×CH$_3$); 3.74 m, 2H (H-2'); 3.76 d, J(CH$_2$—P)=8.3 (CH$_2$—P); 4.19 m, 2H (H-1'); 4.59 m, 2H (P—OCH); 4.75 s, 1H (H-5); 6.65 bs, 2H (NH$_2$); 10.45 s, 1H (OH). $^{13}$C NMR (CD$_3$SOCD$_3$): 23.87 d, 2C, J(CH$_3$,P)=4.9 and 24.01 d, 2C, J(P,C)=3.9 (CH$_3$); 65.03 d, J(P,C)=164.6 (P—C); 65.04 (C-1'); 70.37 d, 2C, J(P,C)=6.3) (P—OC); 70.87 d, J(P,C)=11.7 (C-2'); 79.95 (C-5); 155.68 (C-4); 164.25 (C-2); 171.01 (C-6).

This product was treated with bromotrimethylsilane (10 mL) in acetonitrile (80 mL) overnight, evaporated in vacuo and the residue treated with water (50 mL). After 10 min, conc. aqueous ammonia was added to alkaline reaction and the mixture evaporated. The residue was deionized on a column (100 mL) of Dowex 50×8 and the UV-absorbing ammonia eluate was evaporated to dryness. It was dissolved in minimum hot water by addition of conc. aqueous ammonia and acidified by conc. HCl to pH 3–3.5. The precipitate was collected, washed with water, ethanol and dried in vacuo. Yield, 0.7 g, m.p. 227° C. For $C_7H_{12}N_3O_6P$ (265.16) calculated 31.71% C, 4.56% H, 15.85% N, 11.68% P; found 31.55% C, 4.62% H, 16.15% N, 11.51% P.

EXAMPLE 3

(a) 2,4-Diamino-6-(S)-[2-(phosphonomethoxy)propoxy]pyrimidine (H-3560)

Diisopropyl (S)-2-(4-toluenesulfonyloxy)propyloxymethylphosphonate (25.7 g, 63 mmol) in DMF (40 mL) was added at 90° C. to a stirred mixture of 2,4-diamino-6-hydroxypyrimidine (60 mmol), DMF (40 mL) and DBU (10.6 mL, 60 mmol). The reaction mixture was stirred at 100° C. 24 h and evaporated in vacuo. The residue was taken in chloroform (200 mL), filtered and washed with saturated NaCl (100 mL). The aqueous wash was extracted with chloroform (5×50 mL), the combined extracts were dried with magnesium sulfate and evaporated.

Separation on silica gel column (150 mL) in chloroform by chloroform-ethanol gradient gave the main product (O6-isomer) as an oily residue which was dried in vacuo over phosphorus pentoxide overnight. Acetonitrile (80 mL) and bromotrimethylsilane (20 mL) were added and the solution was left to stand overnight in a stoppered flask. The volatiles were evaporated in vacuo and the residue was treated with water (100 mL). After 10 min, conc. aqueous ammonia was added to alkaline reaction and the mixture was evaporated. The residue was deionized on a column (100 mL) of Dowex 50×8 and the UV-absorbing ammonia eluate was evaporated to dryness. This product in water (20 mL) was made alkaline by conc. aqueous ammonia and applied on a column (200 mL) Dowex 1×2 (acetate form) prewashed with water. Elution with water followed by linear gradient of acetic acid (0–0.5 M, 1.5 L each) gave the main UV-absorbing fraction which was evaporated, the residue codistilled with water (3×50 mL) and crystallized from water. Yield, 3.5 g (19.7%), m.p. 281° C. For monohydrate $C_8H_{15}N_4O_5P \cdot H_2O$ (296.22) calculated 32.44% C, 5.78% H, 18.91% N, 10.46% P; found 32.67% C, 5.86% H, 19.40% N, 10.60% P. $^1$H NMR (D$_2$O+NaOD): 1.26 d, 3H, J(3',2')=6.4 (H-3'); 3.51 dd, 1H, J(CH$_b$,P)=9.4, J(gem)=12.2 (CH$_b$P); 3.60 dd, 1H, J(CH$_a$,P)=9.4, J(gem)=12.2 (CH$_a$P); 3.92 m, 2H (H-2'); 4.06 dd, 1H, J(1'b, 2')=5.5, J(gem)==10.5 (H-1'b); 4.14 dd, 1H, J(1'a,2')=3.7, J(gem)=10.5 (H-1'a); 5.41 s, 1H (H-5). $^{13}$C NMR (D$_2$O): 15.84 (C-3'); 66.99 d, J(CH$_2$—P)=149.9 (P—C); 69.68 (C-1'); 75.14 d, J(2',P)=11.2 (C-2'); 76.84 (C-5); 166.74 (C-2); 162.83 (C-4); 171.05 (C-6).

(b) 2,4-Diamino-6-(R)-[2-(phosphonomethoxy)propoxy]pyrimidine (H-3567)

The (R) enantiomer was prepared analogously to Example 3(a) from isopropyl (R)-2-(4-toluenesulfonyloxy)propyloxymethylphosphonate (50 mmol), 2,4-diamino-6-hydroxypyrimidine (60 mmol) and DBU (60 mmol). in DMF (70 mL). The reaction mixture was stirred at 100° C. 24 h. Further work-up followed the procedure described in Example 4. Yield, 24%, not melting under 290° C. For monohydrate $C_8H_{15}N_4O_5P\cdot H_2O$ (296.22) calculated 32.44% C, 5.78% H, 18.91% N, 10.46% P; found 32.54% C, 5.90% H, 19.10% N, 10.65% P. $^1H$ NMR and $^{13}C$ NMR spectra are identical with those for the (S)-enantiomer.

EXAMPLE 4

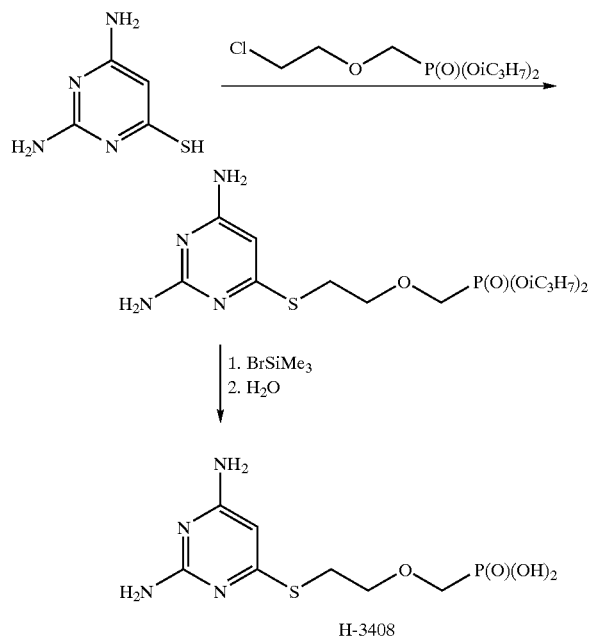

2,4-Diamino-6-[2-(phosphonomethoxy)ethylsulfanyl]pyrimidine

As suspension of 2,4-diamino-6-sulfanylpyrimidine hemisulfate (2.616 g, 13.7 mmol) in DMF (40 mL) was treated with sodium hydride (1.0855 g, 27 mmol, 60% dispersion in paraffin oil) 1 h under stirring, followed by diisopropyl 2-chloroethoxymethylphosphonate (9 mL, 17.2 mmol). The mixture was stirred 8 h at 80° C., filtered through celite pad and evaporated in vacuo. The residue in chloroform was purified on silica gel column (150 mL) in chloroform-ethanol (49:1) to afford 2,4-diamino-6-[2-(diisopropylphosphonylmethoxy)-ethylsulfanyl]pyrimidine (4.0 g, 80%), m.p. 109° C. For $C_{13}H_{25}N_4O_4PS$ (364.40) calculated 42.85% C, 6.91% H, 15.38% N, 8.50% P, 8.80% S; found 42.48% C, 6.94% H, 15.50% N, 8.63% P, 9.01% S. $^1H$ NMR ($CD_3SOCD_3$): 1.24 d, 6H and 1.25 d, 6H, J($CH_3$,CH)=6.1 ($CH_3$); 3.17 t, 2H, J(1',2')=6.6 (H-1'); 3.68 t, 2H, J(2',1')=6.6 (H-2'); 3.77 d, J($CH_2$—P)=8.3 ($CH_2$—P); 4.60 m, 2H (P—OCH); 5.60 s, 1H (H-5); 5.95 brs, 2H and 6.17 brs, 2H ($NH_2$).

This compound in acetonitrile (50 mL) was treated with bromotrimethylsilane (5 mL) overnight and the volatiles were evaporated in vacuo. The residue was treated with water (100 mL). After 10 min, conc. aqueous ammonia was added to alkaline reaction and the mixture was evaporated. The residue was deionized on a column (100 mL) of Dowex 50×8 and the UV-absorbing ammonia eluate was evaporated to dryness. This product in water (20 mL) was made alkaline by conc. aqueous ammonia and applied on a column (100 mL) Dowex 1×2 (acetate form) prewashed with water. Elution with water followed by linear gradient of acetic acid (0–0,5 M, 1.5 L each) gave the main UV-absorbinh fraction which was evaporated, the residue codistilled with water (3×50 mL) and the residue was crystallized from water. Yield, 2.8 g (91%) 2,4-diamino-6-[2-(phosphonomethoxy)ethylsulfanyl]pyrimidine, m.p. 246° C. For $C_7H_{13}N_4O_4PS$ (280.24) calculated 30.00% C, 4.68% H, 19.99% N, 11.05% P, 11.44% S; found 30.27% C, 4.80% H, 19.74% N, 10.98% P, 11.60% S. $^1H$ NMR ($D_2O$+NaOD): 3.18t, 2H, J(1',2')=6.8 (H-1'); 3.56 d, 2H, J($CH_2$,P)=8.7; ($CH_2$P); 3.68 t, 2H, J(2',1')=6.9 (H-2'); 5.70 s, 1H (H-5); 6.32 brs, 2H (2-$NH_2$); 6.48 brs, 2H (4-$NH_2$).

EXAMPLE 5

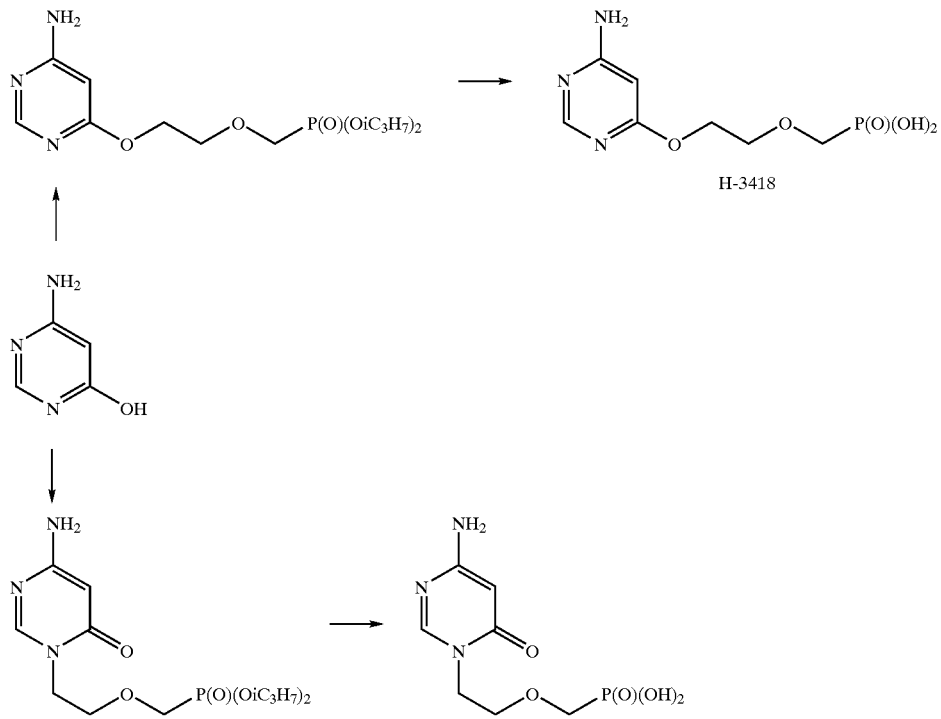

4-Amino-6-[2-(phosphonomethoxy)ethoxy]pyrimidine and 4-amino-1-[2-(phosphonomethoxy)ethyl]pyrimidin-6(1H)-one 4-Amino-6-hydroxy-2-sulfanylpyrimidine (20 g) in boiling ethanol (300 mL) was treated under stirring with Raney-Ni until the starting material disappeared. The supension was filtered while hot, the precipitate washed with hot ethanol (300 mL) and the filtrate evaporated to dryness. The residue afforded on crystallization from ethanol (ether added to turbidity) 4-amino-6-hydroxypyrimidine, m.p. 272° C. Yield, 10.0 g (64.4%). For $C_4H_5N_3O$ (111.10) calculated 43.24% C, 4.54% H, 37.82% N; found 43.40% C, 4.65% H, 38.01% N. Mass spectrum: 112 (MH$^+$). $^1$H-NMR (CD$_3$SOCD$_3$): 4.97 s, 1H (H-5); 6.42 brs, 2H (NH$_2$); 7.77 s, 1H (H-2); 11.41 brs, 1H (OH).

This compound (3.6 g, 33.6 mmol) in DMF (70 mL) was treated with NaH (1.36 g, 34 mmol, 60% dispersion in paraffin oil) 0.5 h under stirring, and diisopropyl 2-chloroethoxymethylphosphonate (9.4 mL, 40.5 mmol) was added. The mixture was stirred 8 h at 80° C., filtered through celite pad and evaporated in vacuo. The residue in chloroform was purified on silica gel; elution with chloroform-ethanol (97.5:2.5) afforded 4-amino-6-[2-(diisopropylphosphonylmethoxy)ethoxy]pyrimidine which was crystallized from ethyl acetate—petroleum ether. Yield, 3.0 g (26.8%), m.p. 112° C. For $C_{13}H_{24}N_3O_5P$ (333.32) calculated 46.84% C, 7.26% H, 12.61% N, 9.29% P; found 46.69% C, 7.38% H, 12.45% N, 9.40% P. $^1$H NMR (CD$_3$SOCD$_3$): 1.22 d, 6H and 1.23 d, 6H, J(CH$_3$,CH)=6.1 (4×CH$_3$); 3.78 brt, 2H, J(2',1')=4.5 (H-2'); 3.78 d, J(CH$_2$—P)=8.4 (CH$_2$—P); 4.31 brt, 2H, J(1',2')=4.5 (H-1'); 4.59 m, 2H (P—OCH); 5.67 s, 1H (H-5); 6.62 bs, 2H (NH$_2$); 8.07 s, 1H (H-2). $^{13}$C NMR (CD$_3$SOCD$_3$): 64.42 (C-1').

This compound was treated with bromotrimethylsilane (10 mL) in acetonitrile (70 mL) overnight at room temperature. After evaporation in vacuo, the residue was treated with water (100 mL). After 10 min, conc. aqueous ammonia was added to alkaline reaction and the mixture was evaporated. The residue was deionized on a column (100 mL) of Dowex 50×8 and the UV-absorbing ammonia eluate was evaporated to dryness. This product in water (20 mL) was made alkaline by conc. aqueous ammonia and applied on a column (150 mL) Dowex 1×2 (acetate form) prewashed with water. Elution with water followed by linear gradient of acetic acid (0–1 M, 1L each) gave the main UV-absorbing fraction which was evaporated, the residue codistilled with water (3×50 mL) and the residue was crystallized from water. Yield, 1.8 g (80%) 4-amino-6-[2-(phosphonomethoxy)ethoxy]pyrimidine, m.p. 254° C. For $C_7H_{12}N_3O_5P$ (249.16) calculated 33.74% C, 4.85% H, 16.86% N, 12.43% P; found 34.02% C, 4.80% H, 16.88% N, 12.58% P.

Further elution of the crude reaction mixture on silica gel column with chloroform-ethanol (95:5) gave the oily 4-amino-1-[2-(diisopropylphosphonyl-methoxy)ethyl]pyrimidin-6(1H)-one which was dried in vacuo. Yield, 4.6 g (41.1%). This compound was treated with bromotrimethylsilane (10 mL) in acetonitrile (70 mL) overnight at room temperature. After evaporation in vacuo, the residue was treated with water (100 mL). After 10 min, conc. aqueous ammonia was added to alkaline reaction and the mixture was evaporated. The residue was applied on a column (100 mL) of Dowex 50×8 and eluted with water. The main UV-absorbing fraction was evaporated and the residue was crystallized from 70% aqueous ethanol (ether added to turbidity). Yield, 2.8 g (91%) 4-amino-1-[2-(phosphonomethoxy)ethyl]pyrimidin-6(1H)-one, m.p. 233° C. For $C_7H_{12}N_3O_5P$ (249.16) calculated 33.74% C, 4.85% H, 16.86% N, 12.43% P; found 34.02% C, 4.80% H, 16.88% N, 12.58% P. $^1$H NMR (CD$_3$SOCD$_3$): 3.56 d, 2H, J(CH$_2$,P)=8.8 (CH$_2$P); 3.64 t, 2H, J(2',1')=4.9 (H-2'); 3.90t, 2H, J(1',2')=4.9 (H-1'); 5.06 s, 1H (H-5); 6.45 brs, 2H (NH$_2$); 6.90 brs, 2H (P—OH); 7.98 s, 1H (H-2). $^{13}$C NMR (CD$_3$SOCD$_3$): 44.44 (C-1').

EXAMPLE 6

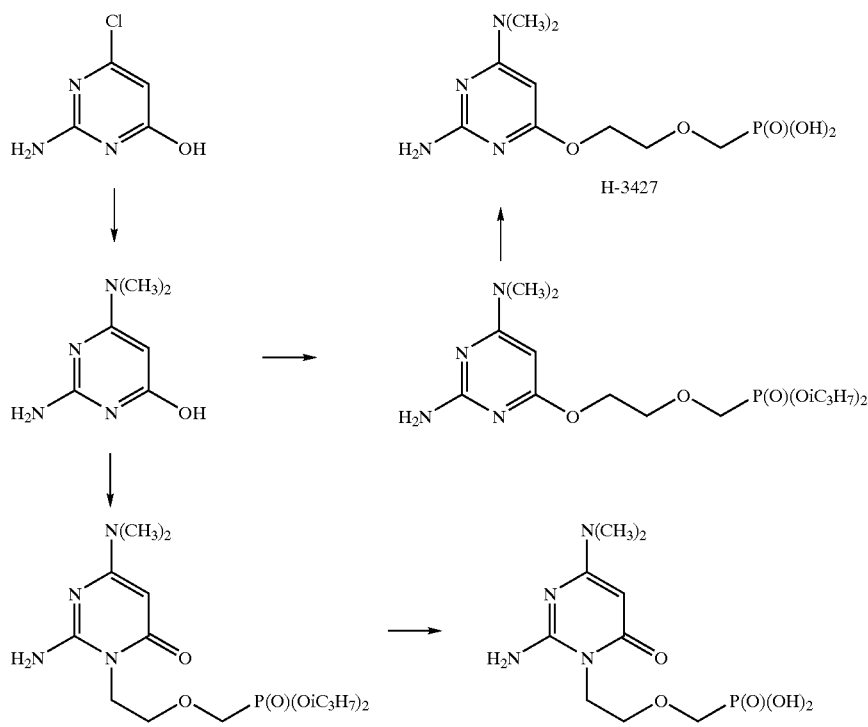

2-Amino-4-dimethylamino-6-[2-(phosphonomethoxy)ethoxy]pyrimidine and 2-Amino-4-dimethylamino-1-[2-(phosphonomethoxy)ethyl]pyrimidin-6(1H)-one 2-Amino-4-chloro-6-hydroxypyrimidine monohydrate (5.0 g) was stirred with 30% dimethylamine in ethanol (180 mL) at 100° C. in an autoclave for 16 h. The crystalline product was filtered, washed with water, acetone, ether and dried in vacuo to afford 2-amino-4-dimethylamino-6-hydroxypyrimidine, not melting under 300° C. Yield, 4.3 g (81%). For $C_6H_{10}N_4O$ (154.17) calculated 46.34% C, 6.54% H, 36.34% N; found 46.38% C, 6.65% H, 36.68% N. $^1$H-NMR (CD$_3$SOCD$_3$): 2.89 s, 6H (N—CH$_3$); 4.51 s, 1H (H-5); 6.18 brs, 2H (NH$_2$); 9.75 brs, 1H (OH).

This compound (4.0 g, 26 mmol) and cesium carbonate (4.22 g, 13 mmol) in DMF (60 mL) were stirred at 100° C. for 1 h and diisopropyl 2-chloroethoxymethylphosphonate (8 mL) was added. The mixture was stirred at 100° C. for 24 h, filtered while hot and evaporated in vacuo. The residue was extracted with hot chloroform (100 mL), filtered and purified by chromatography on silica gel column (200 mL). Elution with chloroform gave 2-amino-4-dimethylamino-6-[2-(diisopropylphosphonylmethoxy)ethoxy]pyrimidine as a thick oil (4.6 g). It was treated with bromotrimethylsilane (5 mL) and acetonitrile (50 mL) overnight at room temperature. After evaporation in vacuo, the residue was treated with water (100 mL). After 10 min, conc. aqueous ammonia was added to alkaline reaction and the mixture was evaporated. The residue was deionized on a column (100 mL) of Dowex 50×8 and the UV-absorbing ammonia eluate was evaporated to dryness. This product in water (20 mL) was made alkaline by conc. aqueous ammonia and applied on a column (150 mL) Dowex 1×2 (acetate form) prewashed with water. Elution with water followed by linear gradient of acetic acid (0–0.4 M, 1L each) gave the main UV-absorbing fraction which was evaporated, the residue codistilled with water (3×50 mL) and the residue was crystallized from water. Yield, 1.1 g 2-amino-4-dimethylamino-6-[2-(phosphonomethoxy)ethoxy]pyrimidine, m.p. 168° C. For $C_9H_{17}N_4O_5P$ (292.23) calculated 36.99% C, 5.86% H, 19.17% N, 10.60% P; found 37.05% C, 5.80% H, 18.98% N, 10.51% P. $^1$H NMR (DMSO): 6.69 bs, 2H (NH$_2$); 4.69 s, 1H (H-5); 3.98 t, J=6.0 Hz, 2H (2×H-1'); 3.61 t, J=6.0 Hz, 2H (2×H-2'); 3.59 d, 2H, J(H,P)=8.3 Hz (P—CH$_2$); 2.89 s, 6H (N(CH$_3$)$_2$). $^{13}$C NMR (DMSO): 162.37, 161.94 and 154.67 (C-2, C-4 and C-6); 75.79 (C-5); 69.82 d, J(C,P)=10.3 Hz (C-2'); 66.76 d, J(C,P)=158.7 Hz (P—CH$_2$); ~40.0 (C-1', overlapped with DMSO); 36.93 (N(CH$_3$)$_2$).

Further elution of the silica gel column with chloroform-ethanol gradient afforded 2-amino-4-dimethylamino-1-[2-(diisopropylphosphonylmethoxy)ethyl]pyrimidin-6(1H)-one as a thick oil (2.0 g) which was treated with bromotrimethylsilane (5 mL) and acetonitrile (50 mL) overnight and worked up similarly. After Dowex 1 chromatography, the product gave on crystallization from water 2-amino-4-dimethylamino-1-[2-(phosphonomethoxy)ethyl]pyrimidin-6(1H)-one, m.p. 235° C. For $C_9H_{17}N_4O_5P$ (292.23) calculated 36.99% C, 5.86% H, 19.17% N, 10.60% P; found 37.15% C, 5.92% H, 19.28% N, 10.66% P. $^1$H NMR (DMSO): 6.03 bs, 2H (NH$_2$); 5.20 s, 1H (H-5); 4.26 m, 2H (2×H-1'); 3.74 m, 2H (2×H-2'); 3.58 d, 2H, J(H,P)=8.8 Hz (P—CH$_2$); 2.93 s, 6H (N(CH$_3$)$_2$). $^{13}$C NMR (DMSO): 169.93, 164.91 and 161.92 (C-2, C-4 and C-6); 75.02 (C-5); 70.89 d, J(C,P)=11.4 Hz (C-2'); 66.96 d, J(C,P)=160.7 Hz (P—CH$_2$); 64.28 (C-1'); 36.95 (N(CH$_3$)$_2$).

EXAMPLE 7

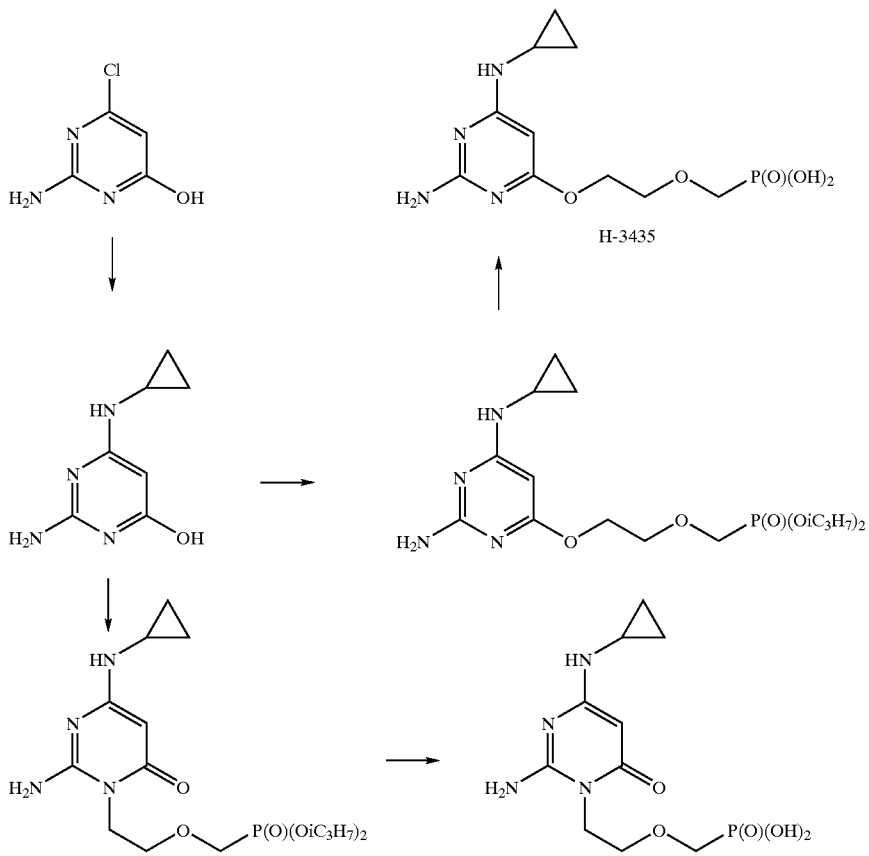

2-Amino-4-cyclopropylamino-6-[2-(phosphonomethoxy)ethoxy]pyrimidine and 2-Amino-4-cyclopropylamino-1-[2-(phosphonomethoxy)ethyl]pyrimidin-6(1H)-one 2-Amino-4-chloro-6-hydroxypyrimidine monohydrate (5.0 g) was refluxed in ethanol (150 mL) with cyclopropylamine for 12 h. The mixture was evaporated in vacuo, codistilled with ethanol (3×50 mL), adsorbed from methanol on silica gel and applied on a column of silica gel (200 mL) in chloroform. Elution with chloroform-ethanol gradient afforded crystalline product which was filtered from ether and dried in vacuo to afford 2-amino-4-cyclopropylamino-6-hydroxypyrimidine, m.p.229° C. Yield, 3.0 g. For $C_7H_{10}N_4O$ (166.18) calculated 50.59% C, 6.07% H, 33.71% N; found 50.49% C, 6.25% H, 33.61% N. $^1H$ NMR (DMSO): 9.73 brs, 1H (OH); 6.55 bs, 2H (NH); 6.08 brs, 2H (NH$_2$); 4.66 s, 1H (H-5); 2.30 m, 1H and 0.62 m, 2H and 0.40, m, 2H (C—CH$_2$, N—CH).

The mixture of this compound (3.0 g, 18 mmol) and cesium carbonate (2.92 g, 9 mmol) in DMF (50 mL) was stirred at 100° C. for 1 h and diisopropyl 2-chloroethoxymethylphosphonate (6 mL) was added. The reaction mixture was stirred at 100° C. for 24 h, filtered while hot and evaporated in vacuo. The residue was extracted with hot chloroform (100 mL), filtered, concentrated in vacuo and purified by chromatography on silica gel column (2×200 mL). Elution with chloroform gave 2-amino-4-cyclopropylamino-6-[2-(diisopropylphosphonylmethoxy)ethoxy]pyrimidine as a thick oil (1.8 g). It was treated with bromotri-methylsilane (5 mL) and acetonitrile (50 mL) overnight at room temperature. After evaporation in vacuo, the residue was treated with water (100 mL). After 10 min, conc. aqueous ammonia was added to alkaline reaction and the mixture was evaporated. The residue was deionized on a column (100 mL) of Dowex 50×8 and the UV-absorbing ammonia eluate was evaporated to dryness. This product in water (20 mL) was made alkaline by conc. aqueous ammonia and applied on a column (150 mL) Dowex 1×2 (acetate form) prewashed with water. Elution with water followed by linear gradient of acetic acid (0–0.4 M, 1L each) gave the main UV-absorbing fraction which was evaporated, the residue codistilled with water (3×50 mL) and the residue was crystallized from water. Yield, 1.0 g 2-amino-4-cyclopropylamino-6-[2-(phosphonomethoxy)ethoxy]pyrimidine, m.p. 244° C. For $C_{10}H_{17}N_4O_5P$ (304.24) calculated 39.48% C, 5.63% H, 18.42% N, 10.18% P; found 39.65% C, 5.70% H, 18.59% N, 10.11% P. $^1H$ NMR (D$_2$O+NaOD): 0.54 m, 2H and 0.80 m, 2H (C—CH$_2$); 2.53 m, 1H (N—CH); 3.57 d, 2H, J(CH$_2$,P)=8.4 (CH$_2$P); 3.91 m, 2H (H-2'); 4.32 m, 2H (H-1'); 5.61 s, 1H (H-5).

Further elution of the silica gel column with chloroform-ethanol gradient afforded (after crystallization from ethanol-ether) yellow 2-amino-4-cyclopropylamino-1-[2-(diisopropylphosphonylmethoxy)ethyl]pyrimidin-6(1H)-one (1.6 g) which was treated with bromotrimethylsilane (5 mL) and acetonitrile (50 mL) overnight and worked up similarly. On Dowex 50 chromatography, the product was eluted with water and evaporated in vacuo. The residue gave on crystallization from water 2-amino-4-cyclopropylamino-1-[2-(phosphono-methoxy)ethyl]pyrimidin-2-one, not melting under 290° C. Yield, 0.90 g. For $C_{10}H_{17}N_4O_5P$ (304.24) calculated 39.48% C, 5.63% H, 18.42% N, 10.18% P; found 39.70% C, 5.78% H, 18.69% N, 10.32% P. $^{13}C$ NMR (D$_2$O+NaOD): 173.71, 170.07 and 165.53 (C-2, C-4 and C-6); 78.75 (C-5); 73.31 d, J(C,P)=10.3 Hz (C-2'); 72.19 J(C,P)=149.4 Hz (P—CH$_2$); 69.14 (C-1'); 25.96 (N—CH); 9.43 (2×CH$_2$ of cyclopropyl).

EXAMPLE 8

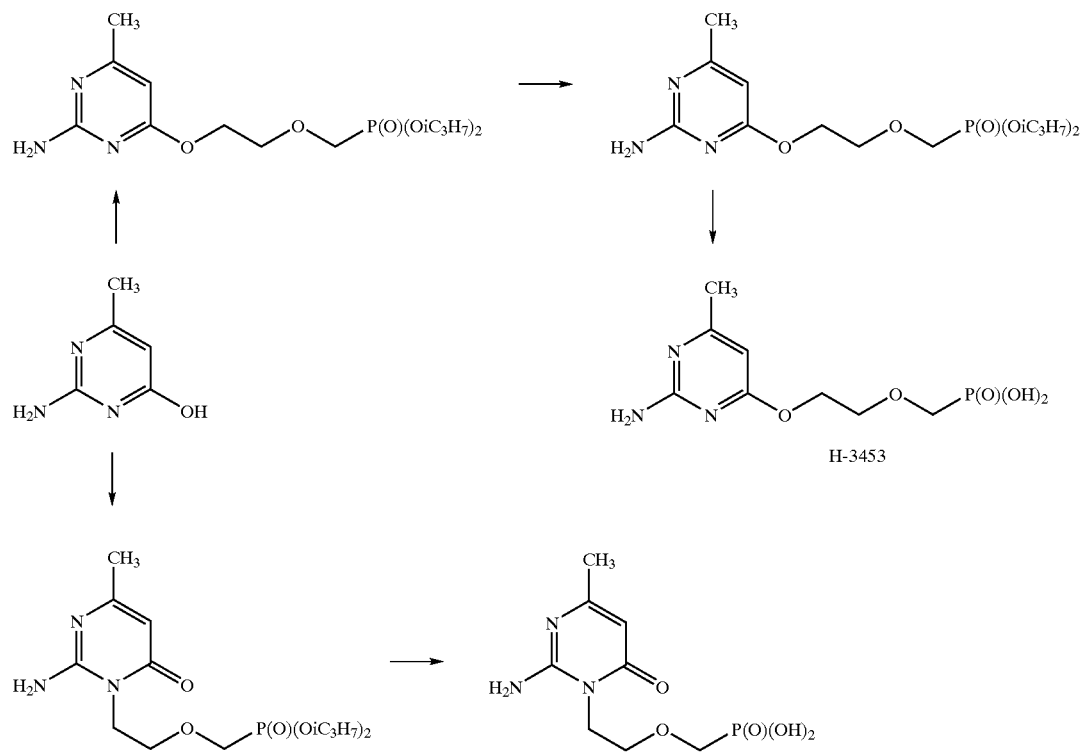

H-3453

2-Amino-4-methyl-6-[2-(phosphonomethoxy) ethoxy]pyrimidine and 2-Amino-4-methyl-1-[2-(phosphonomethoxy)ethyl]pyrimidin-6(1H)-one Diisopropyl 2-chloroethoxymethylphosphonate (15 mL, 62.5 mmol) was added to a mixture of 2-amino-6-hydroxy-4-methylpyrimidine (6.25 g, 50 mmol) and cesium carbonate (11.3 g, 25 mmol) in DMF (70 mL) which has been prior to addition stirred at 100° C. for 1 h. The reaction mixture was then stirred at 100° C. for 14 h, filtered while hot and evaporated in vacuo. The residue gave on extraction with chloroform and subsequent purification on silica gel column (250 mL) 2-amino-4-methyl-6-[2-(diisopropylphosphonyl-methoxy)ethoxy]pyrimidine which was crystallized from ethyl acetate—petroleum ether. Yield, 5.75 g, m.p. 72–73° C. For $C_{14}H_{26}N_3O_5P$ (347.35) calculated 48.41% C, 7.54% H, 12.10% N, 8.92% P; found 48.70% C, 7.60% H, 12.32% N, 9.14% P. $^1$H NMR (CDCl$_3$): 5.95 q, 1H, J=0.6 Hz (H-5); 4.90 b, 2H (NH$_2$); 4.76 dh, 2H, J(H,P)=7.6 Hz and J(H,H)=6.2 Hz (2×OCH (iPr)); 4.42 m, 2H (2×H-1'); 3.90 m, 2H (2×H-2'); 3.82 d, 2H, J(H,P)=8.2 Hz (P—CH$_2$); 2.26 d, 3H, J=0.6 Hz (CH$_3$); 1.34 d, 6H, J=6.2 Hz and 1.33 d, 6H, J=6.2 Hz (4×CH$_3$ (iPr)). $^{13}$C NMR (CDCl$_3$): 170.36, 168.27 and 162.48 (C-2, C-4 and C-6); 97.03 (C-5); 71.17 d, J(C,P)=10.8 Hz (C-2'); 71.06 d, J(C,P)=6.8 Hz (OCH (iPr)); 65.99 d, J(C,P)=167.6 Hz (P—CH$_2$); 64.60 (C-1'); 24.04 d, J(C,P)=3.9 Hz and 23.90 d, J(C,P)=4.9 Hz (4×CH$_3$ (iPr)); 23.61 (CH$_3$).

This compound was treated with bromotrimethylsilane (5 mL) in acetonitrile (50 mL) at room temperature overnight and the volatiles were evaporated in vacuo. The residue was dissolved in water (100 mL), conc. aqueous ammonia was added to alkaline reaction and the mixture was evaporated. The residue was deionized on a column (100 mL) of Dowex 50×8 and the UV-absorbing ammonia eluate was evaporated to dryness. This product in water (20 mL) was made alkaline by conc. aqueous ammonia and applied on a column (150 mL) Dowex 1×2 (acetate form) prewashed with water. Elution with water followed by linear gradient of acetic acid (0–0.4 M, 1L each) gave the main UV-absorbing fraction which was evaporated, the residue codistilled with water (3×50 mL) and the residue was crystallized from water. Yield, 3.67 g 2-amino-4-methyl-6-[2-(phosphonomethoxy) ethoxy]pyrimidine, m.p. 245° C. For $C_8H_{14}N_3O_5P$ (263.19) calculated 36.51% C, 5.36% H, 15.97% N, 11.77% P; found 36.65% C, 5.60% H, 15.69% N, 11.92% P. $^1$H NMR (D$_2$O+NaOD): 6.13 s, 1H (H-5); 4.39 m, 2H (2×H-1'); 3.92 m, 2H (2×H-2'); 3.57 d, 2H, J(H,P)=8.5 Hz (P—CH$_2$); 2.26 s, 3H (CH$_3$). $^{13}$C NMR (D$_2$O+NaOD): 173.63, 172.80 and 165.50 (C-2, C-4 and C-6); 98.75 (C-5); 73.09 d, J(C,P)=10.2 Hz (C-2'); 72.06 d, J(C,P)=149.4 Hz (P—CH$_2$); 68.85 (C-1'); 25.42 (CH$_3$).

Further elution of the silica gel column followed by crystallization from ethyl acetate—petroleum ether gave 2-amino-4-methyl-1-[2-(diisopropylphosphonylmethoxy) ethyl]pyrimidin-6(1H)-one (4.2 g), m.p. 88° C. For $C_{14}H_{26}N_3O_5P$ (347.35) calculated 48.41% C, 7.54% H, 12.10% N, 8.92% P; found 48.49% C, 7.62% H, 12.30% N, 9.08% P. $^1$H NMR (CDCl$_3$): 5.79 q, 1H, J=0.8 Hz (H-5); 5.62 b, 2H (NH$_2$); 4.72 dh, 2H, J(H,P)=7.6 Hz and J(H,H)=6.2 Hz (2×OCH (iPr)); 4.20 m, 2H (2×H-1'); 3.90 m, 2H (2×H-2'); 3.74 d, 2H, J(H,P)=8.6 Hz (P—CH$_2$); 2.12 d, 3H, J=0.8 Hz (CH$_3$); 1.32 d, 6H, J=6.2 Hz and 1.29 d, 6H, J=6.2 Hz (4×CH$_3$ (iPr)). $^{13}$C NMR (CDCl$_3$): 164.33, 162.93 and 156.37 (C-2, C-4 and C-6); 102.22 (C-5); 72.88 d, J(C,P)=11.7 Hz (C-2'); 71.27 d, J(C,P)=6.8 Hz (OCH (iPr)); 66.17 d, J(C,P)=168.1 Hz (P—CH$_2$); 43.06 (C-1'); 23.97 d, J(C,P)=3.9 Hz and 23.91 d, J(C,P)=4.9 Hz (2×CH$_3$ (iPr)); 23.64 (CH$_3$).

This product was treated analogously with bromotrimethylsilane (5 mL) in acetonitrile (50 mL) to afford, after chromatography of the deionized reaction mixture on Dowex 1×2 and crystallization from water, 2-amino-4-methyl-1-[2-(phosphonomethoxy)ethyl]pyrimidin-6(1H)-one. Yield, 2.3 g, m.p. 283° C. For $C_8H_{14}N_3O_5P$ (263.19) calculated 36.51% C, 5.36% H, 15.97% N, 11.77% P; found 36.40% C, 5.23% H, 15.77% N, 12.00% P. $^1$H NMR (D$_2$O+NaOD): 5.77 s, 1H (H-5); 4.18 t, 2H, J=5.3 Hz (2×H-1'); 3.82 t, 2H, J=5.3 Hz (2×H-2'); 3.50 d, 2H, J(H,P)=8.7 Hz (P—CH$_2$); 2.12 s, 3H (CH$_3$). $^{13}$C NMR (D$_2$O+NaOD): 169.48, 168.32 and 160.25 (C-2, C-4 and C-6); 102.40 (C-5); 73.17 (C-2'); 72.55 d, J(C,P)=142.0 Hz (P—CH$_2$); 45.60 (C-1'); 25.43 (CH$_3$).

EXAMPLE 9

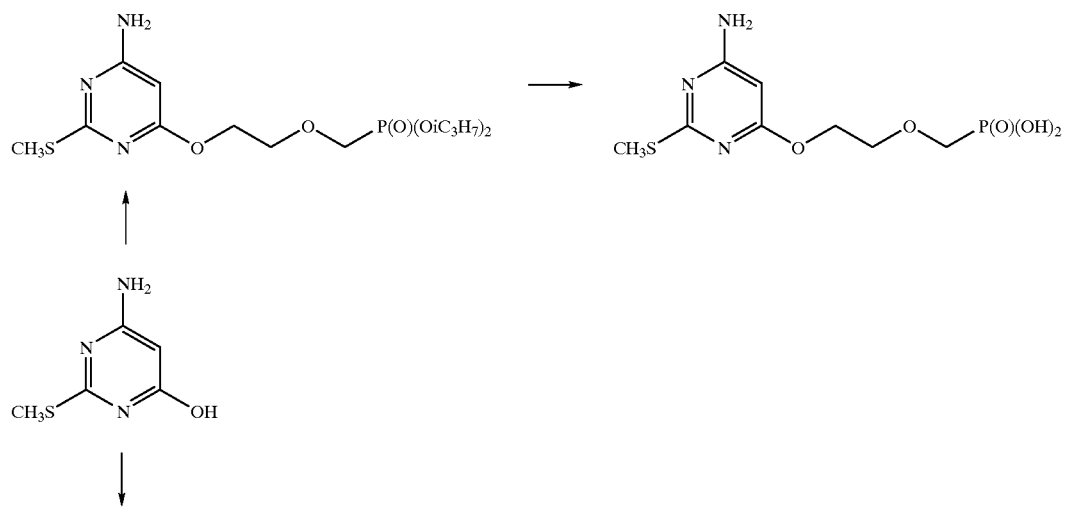

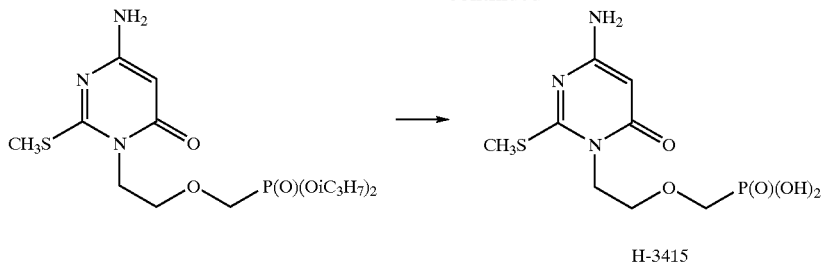

H-3415

4-Amino-2-methylsulfanyl-6-[2-(phosphonomethoxy)ethoxy]pyrimidine

Diethyl 2-hydroxyethylphosphonate (5.3 g, 25 mmol) in DMF (40 mL) was treated at 0° C. with NaH (1.0 g, 60% dispersion in paraffin oil) and, after 1 h stirring at 0° C., 4-amino-6-chloro-2-methylsulfanylpyrimidine (3.5 g, 20 mmol) was added in one portion. The mixture was stirred 16 h at 100° C., evaporated to dryness in vacuo and extracted with hot chloroform (300 mL). The extract was evaporated in vacuo and the residue was treated with bromotrimethylsilane (10 mL) in acetonitrile (50 mL) at room temperature overnight. The mixture was evaporated to dryness in vacuo and the residue was deionized on a column (100 mL) of Dowex 50×8 and the UV-absorbing ammonia eluate evaporated to dryness. This product in water (20 mL) was dissolved by addition of conc. aqueous ammonia and acidified by HCl to pH 3–3.5. The precipitate was collected, washed with water, ethanol and dried in vacuo. Yield, 0.8 g 4-amino-2-methylsulfanyl-6-[2-(phosphonomethoxy)ethoxy] pyrimidine, m.p. 210–211° C. For $C_8H_{14}N_3O_5P$ (263.19) calculated 32.54% C, 4.78% H, 14.23% N, 10.49% P, 10.86% S; found 32.42% C, 4.93% H, 14.07% N, 10.62% P, 11.04% S. $^1H$ NMR ($D_2O$): 5.68 s, 1H (H-5); 4.36 m, 2H (2×H-1'); 3.94 m, 2H (2×H-2'); 3.72 d, 2H, J(H,P)=8.5 (P—$CH_2$); 2.48 s, 3H ($SCH_3$). $^{13}C$ NMR ($D_2O$): 173.70, 172.13 and 167.93 (C-2, C-4 and C-6); 84.82 (C-5); 73.53 d, J(C,P)=10.7 Hz (C-2'); 70.01 d, J(C,P)=156.3 Hz (P—$CH_2$); 69.20 (C-1'); 16.02 ($SCH_3$).

EXAMPLE 10

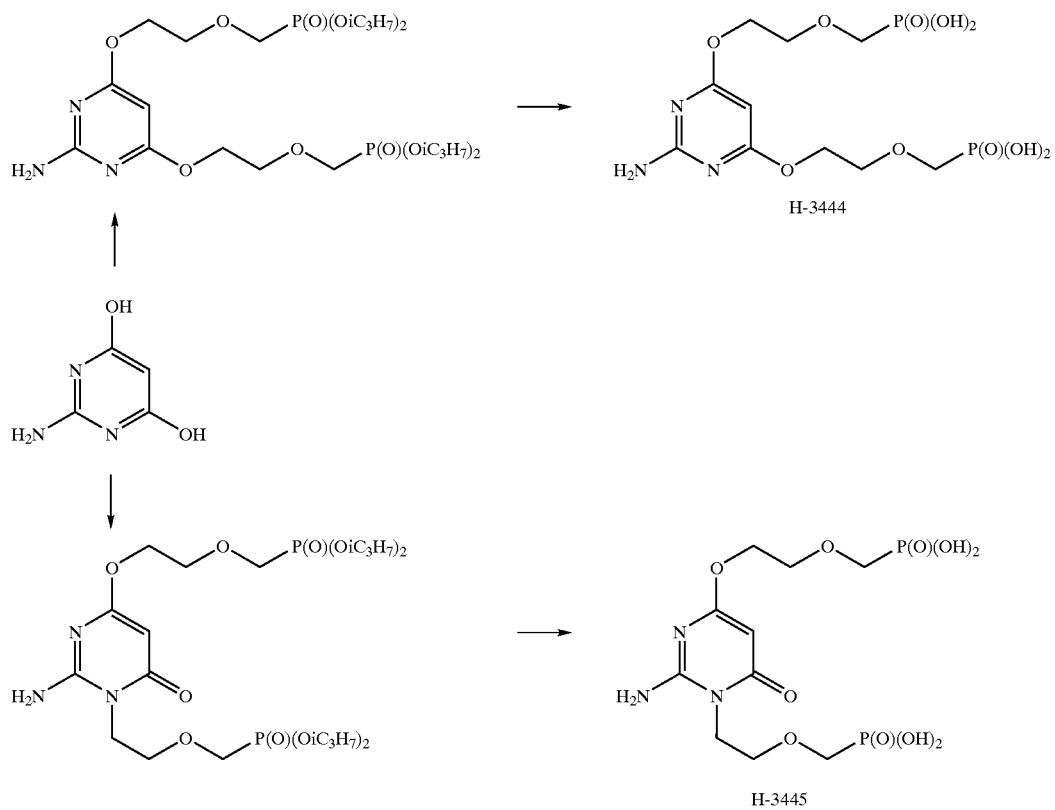

H-3444

H-3445

2-Amino-4,6-bis[2-(phosphonomethoxy)ethoxy]pyrimidine and 2-Amino-4-[2-(phosphonomethoxy)ethoxy]-1-[2-(phosphonomethoxy)ethyl]pyrimidin-6 (1H)-one 2-Amino-4,6-dihydroxypyrimidine (12.7 g, 0.1 mol) and cesium carbonate (27.8 g (85 mmol) in DMF (200 mL) were stirred 1 h at 100° C. and diisopropyl 2-chloroethoxymethylphos (30 mL) was added. The mixture was stirred 16 h at 100° C., filtered while hot and evaporated in vacuo. The residue was purified by silica gel chromatography (200 mL column) to afford 2.8 g of the oily residue which was then treated with bromotrimethylsilane (7 mL) in acetonitrile (50 mL) overnight. The residue was dissolved in water (100 mL), conc. aqueous ammonia was added to alkaline reaction and the mixture was evaporated. The residue was deionized on a column (100 mL) of Dowex 50×8 and the UV-absorbing ammonia eluate was evaporated to dryness. This product was codistilled with ethanol and filtered from ethanol. Yield, 1.4 g 2-amino-4,6-bis[2-(phosphonomethoxy)ethoxy]pyrimidine, m.p.127° C. For $C_{10}H_{19}N_3O_{10}P_2$ (403.22) calculated 29.79% C, 4.75% H, 10.42% N, 15.36% P; found 29.90% C, 4.87% H, 10.24% N, 15.64% P. $^1$H NMR (DMSO): 6.55 b, 2H (NH$_2$); 5.36 s, 1H (H-5); 4.29 m, 2H (2×H-1'); 3.76 m, 2H (2×H-2'); 3.58 d, 2H, J(H,P)=8.6 Hz (P—CH$_2$). $^{13}$C NMR (DMSO): 171.30 (C-4, C-6), 162.76 (C-2); 78.60 (C-5); 70.70 d, J(C,P)=11.7 Hz (C-2'); 66.86 d, J(C,P)=160.2 Hz (P—CH$_2$); 64.81 (C-1').

Further elution of the silica gel column gave thick oil (4.8 g) which was treated with bromotrimethylsilane (10 mL) in acetonitrile (70 mL) overnight and evaporated in vacuo. The residue was passed through Dowex 50×8 column (H$^+$-form) (150 mL) and the column was eluted with water. After washing out the inorganic acids, the product eluted with retention. Its fraction was evaporated and the residue stirred with ethanol-aceton mixture (1:1, 100 mL). The yellowish product was filtered, washed with ether and dried. Yield, 1.8 g 2-amino-4-[2-(phosphonomethoxy)ethoxy]-1-[2-(phosphonomethoxy)ethyl]pyrimidin-6(1H)-one, m.p.108° C. For $C_{10}H_{19}N_3O_{10}P_2$ (403.22) calculated 29.79% C, 4.75% H, 10.42N, 15.36% P; found 29.90% C, 4.87% H, 10.24% N, 15.64% P.

EXAMPLE 11 stirred 6 h at 80° C. The reaction mixture was cooled, diluted with water (200 mL) and passed through a column (200 mL) of Dowex 50×8 in acid cycle. The column was washed with water (1 L) and the resin was suspended in water (300 mL). This suspension was made alkaline with conc. aqueous ammonia, filtered and the resin washed with boiling water (1 L). The combined filtrates were evaporated to dryness and the residue was crystallized from water to afford 2,4-diamino-6-(2-hydroxyethoxy)pyrimidine, m.p. 190° C. Yield, 2.3 g (79.4%). For $C_6H_{10}N_4O_2$ (170.18) calculated 42.34% C, 5.92% H, 30.37% N; found 42.09% C, 5.89% H, 30.63% N. Mass spectrum: 171.3 (MH$^+$). $^1$H NMR (CD$_3$SOCD$_3$): 3.67 br q, 2H, J(CH$_2$,CH$_2$)~J(CH$_2$,OH)=4.8 (O—CH$_2$); 4.10 t, 2H, J(CH$_2$,CH$_2$)=5.0 (O—CH$_2$); 4.79 t, 1H, J(OH,CH$_2$)=4.5 (OH); 5.05 s, 1H (H-5); 5.89 br s, 2H and 6.01 br s, 2H (NH$_2$).

This compound (4.25 g, 25 mmol) and diisopropyl p-toluenesulfonyloxymethylphosphonate (8.75 g, 25 mmol) in DMF (50 mL) was treated with 60% NaH (3.5 g, 3.5 equivalents). The mixture was stirred at ambient temperature for 3 days and acetic acid (4 mL) was added dropwise. The solvent was stripped off in vacuo and the residue extracted with chloroform. The reaction product was purified by silica gel column chromatography to afford, after crystallization from ethyl acetate—petroleum ether, 2,4-diamino-6-[2-(diisopropylphosphonylmethoxy)ethoxy]pyrimidine, m.p. 159° C. Yield, 6.45 g (74%). For $C_{13}H_{25}N_4O_5P$ (348.3) calculated 44.83% C, 7.23% H, 16.08% N, 8.89% P; found 44.86% C, 7.15% H, 16.21% N, 9.05% P. Mass spectrum: 349.3 (MH$^+$). $^1$H NMR spectrum (CD$_3$SOCD$_3$) is identical with that described in Example 1.

Conversion of this compound to 2,4-diamino-6-[2-(phosphonomethoxy)ethoxy]pyrimidine was performed essentially as described in Example 1 and afforded compound identical with this authentic material according to NMR and mass-spectra.

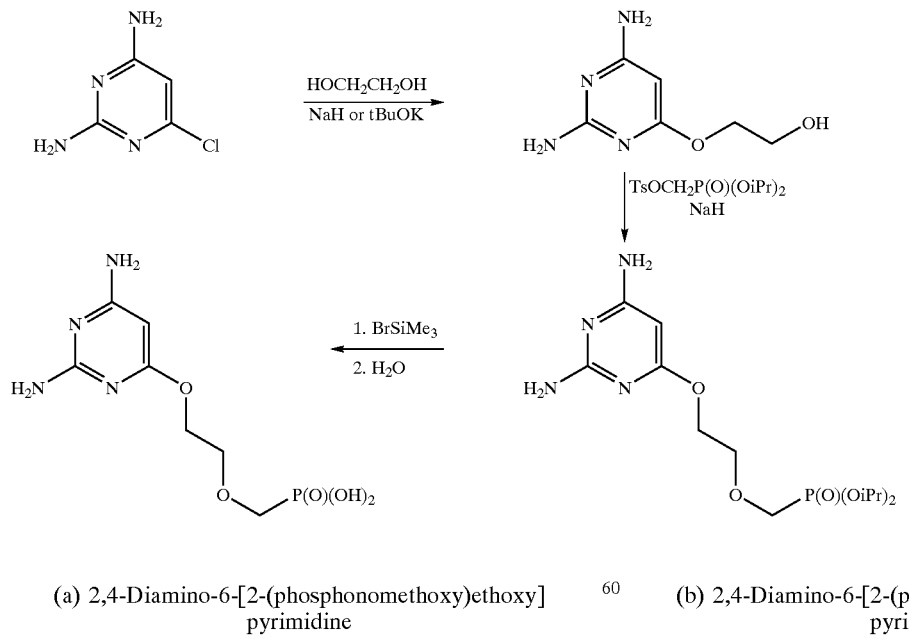

(a) 2,4-Diamino-6-[2-(phosphonomethoxy)ethoxy]pyrimidine (b) 2,4-Diamino-6-[2-(phosphonomethoxy)ethoxy]pyrimidine Sodium hydride (60% suspension in paraffin oil) (2.4 g, 60 mmol) was cautiously added portionwise to redistilled ethylene glycol (50 mL) under exclusion of moisture till dissolution. 2,4-Diamino-6-chloropyrimidine (2.89 g, 20 mmol) was then added in one portion and the mixture was The reaction was performed essentially as described under (a) except that NaH was replaced by the same molar amount of potassium tert-butoxide. Yield of 2,4-diamino-6-(2-hydroxyethoxy)pyrimidine was 81%. Further procedure remained unchanged.

EXAMPLE 12

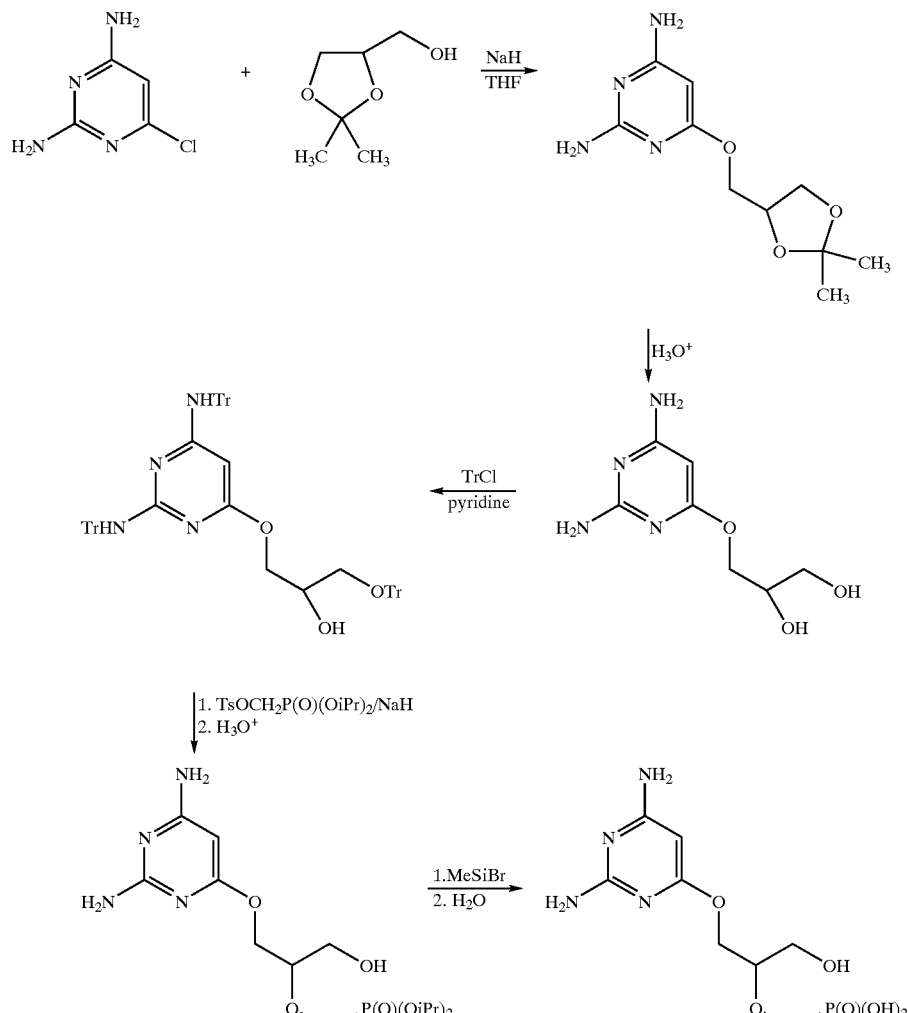

Tr ... $(C_6H_5)_3C$
Ts ... p-toluenesulfonyl
iPr ... isopopyl (a) 2,4-Diamino-6-[(RS)-3-hydroxy-2-(phosphonomethoxy)propoxy]pyrimidine 4-Hydroxymethyl-2,2-dimethyl-1,3-dioxolane (13.2 g, 0.1 mol) in freshly redistilled tetrahydrofuran (100 mL) was added dropwise into a supension of NaH (0.2 mol) in tetrahydrofuran (400 mL). The mixture was stirred till dissolution and 2,4-diamino-6-chloropyrimidine (14.46 g, 0.1 mol) was added. The reaction mixture was refluxed under stirring in an argon atmosphere for 12 h and neutralized with acetic acid. The slurry was filtered, washed with tetrahydrofuran and the filtrate evaporated to dryness in vacuo. Purification on a silica gel column (300 mL) in chloroform gave, after crystallization from ethyl acetate—petroleum ether, 2,4-diamino-6-[2,2-dimethyl-1,3-dioxolanyl-4-methoxy]pyrimidine, m.p. 128° C. Yield, 16.0 g (66.6%). For $C_{10}H_{16}N_4O_3$ (240.3) calculated 49.99% C, 6.71% H, 23.32% N; found 49.95% C, 6.84% H, 23.05% N. Mass spectrum: 241.3 (MH$^+$). $^1$H NMR (CD$_3$SOCD$_3$): 1.27 s, 3H and 1.33 s, 3H (CH$_3$); 3.68 dd, 1H, J(3'b,2')=6.2, J(gem)=8.3 (H-3'b); 4.02 dd, 1H, J(3'a,2')=6.6, J(gem)=8.3 (H-3'a); 4.19 m, 2H (H-1'a); 4.10 dd, 1H, J(1'b,2')=6.0, J(gem)=11.0 (H-1'b); 4.13 dd, 1H, J(1'a,2')=5.0, J(gem)=11.0 (H-1'a); 4.30 m, 1H (H-2'); 5.06 s, 1H (H-5); 5.94 br s, 2H and 6.06 br s, 2H (NH$_2$). $^{13}$C NMR (CD$_3$SOCD$_3$): 25.75 and 26.94 (CH$_3$); 65.72 (C-3'); 66.22 (C-1'); 74.00 (C-2'); 76.58 (C-5); 109.06 (C$_{iPr}$); 163.23 and 166.38 and 170.11 (C-6, C-2, C-4).

This compound (14.4 g, 60 mmol) in 0.25 M H$_2$SO$_4$ (250 mL) was left to stand overnight at room temperature. The mixture was neutralized by saturated barium hydroxide solution, filtered, and the filtrate evaporated to dryness. The residue gave on recrystalization from 90% ethanol (ether added to turbidity) 2,4-diamino-6-(2,3-dihydroxypropoxy)pyrimidine, m.p. 160° C. Yield, 10.0 g (83.3%). For $C_7H_{12}N_4O_3$ (200.2) calculated 42.00% C, 6.04% H, 27.99% N; found 41.84% C, 6.24% H, 28.06% N. Mass spectrum: 201.2 (MH$^+$). $^1$H NMR (CD$_3$SOCD$_3$): 3.40 d, 2H, J(3',2')=5.4 (H-3'); 3.72 m, 1H (H-2'); 4.01 dd, 1H, J(1'b,2')=6.2, J(gem)=10.9 (H-1'b); 4.10 dd, 1H, J(1'a,2')=4.4, J(gem)=10.9 (H-1'a); 4.73 br s, 1H and 5.02 br s, 1H, (OH); 5.09 s, 1H (H-5); 5.99 br s, 2H and 6.07 br s, 2H (NH$_2$). $^{13}$C NMR (CD$_3$SOCD$_3$): 63.14 (C-3'); 67.16 (C-1'); 70.28 (C-2'); 76.64 (C-5); 163.19 and 166.27 (C-2, C-4); 170.62 (C-6).

The mixture of this compound (8.0 g, 40 mmol), trityl chloride (36.4 g, 131 mmol) and 4-dimethylaminopyridine (2 g) in pyridine (160 mL) was stirred 15 h at 50° C. and poured slowly under stirring to water (2 L). The slurry was stirred for 1 h, decanted, and, after stirring with fresh portion of water (2L) it was filtered and washed with water. The precipitate was taken up in chloroform (600 mL), dried with $MgSO_4$ evaporated and codistilled with toluene (3×100 mL portions) in vacuo. The resulting gum was dissolved in minimum volume of ether and dropped, under vigorous stirring, to petroleum ether (1 L). The precipitate was filtered, washed with petroleum ether and dried. Yield, 33.4 g (91.5%) of 6-[2-hydroxy-3-(trityloxy)propoxy]-2,4-bis (tritylamino)pyrimidine, m.p. 138° C. For $C_{64}H_{54}N_4O_2$ (911.1) calculated 6.15% N; found 5.96% N. This trityl derivative (27.3 g, 30 mmol) and diisopropyl p-toluenesulfonyloxymethylphosphonate (15.75 g, 45 mmol) in tetrahydrofuran (300 mL) was treated with 60% NaH (5.4 g, 3.5 equivalents). The mixture was stirred at ambient temperature for 3 days and neutralized with acetic acid. The solvent was stripped off in vacuo, the residue dissolved in ethyl acetate (800 mL) and extracted with water (3×200 mL). The organic phase was evaporated to dryness and the residue refluxed in 80% aqueous acetic acid (300 mL) for 30 min, cooled and evaporated in vacuo. Water (300 mL) was added and the mixture extracted with ether (4×100 mL). The aqueous phase was freed of volatiles in vacuo and applied on a Dowex 50×8 column (200 mL) in acidic form. The column was washed with water till the drop of acidity and UV-absorbance and then eluted with 2.5% aqueous ammonia. The UV-absorbing ammonia eluate was collected, evaporated to dryness in vacuo, the residue codistilled with ethanol (3×100 mL) and dried over $P_2O_5$ in vacuo overnight. Acetonitrile (100 mL) and bromotrimethylsilane (30 mL) were added and the mixture was left to stand overnight under exclusion of moisture. After evaporation of the volatiles in vacuo, water (200 mL) was added to the residue, followed by conc. aqueous ammonia to an alkaline reaction. This solution was evaporated to dryness and the residue deionized on a Dowex 50×8 column (200 mL) under essentially the same conditions. The UV-absorbing ammonia eluate was taken down in vacuo, the residue was dissolved in minimum water and alkalized to pH 10 by ammonia. This solution was applied on a column (200 mL) Dowex 1×2 (acetate form) prewashed with water. The column was washed with water till the drop of UV-absorbance of the eluate and then with linear gradient of acetic acid (0–0,3 M, 1.5 l each). The main UV-absorbing fraction was collected, evaporated in vacuo and the residue codistilled with water (2×100 mL). Crystallization of the residue from water gave 2,4-diamino-6-[(RS)-3-hydroxy-2-(phosphonomethoxy)propoxy]pyrimidine as monohydrate. Yield, 3.8 g (40.6%), white needles, m.p. 213° C. For $C_8H_{15}N_4O_6P.H_2O$ (312.2) calculated 30.78% C, 5.49% H, 17.94% N, 9.92% P; found 30.98% C, 5.52% H, 17.99% N, 9.82% P. Mass spectrum: 295.0 ($MH^+$). $^1H$ NMR ($D_2O$+NaOD): 3.48 dd, 1H, J(P,CHb)=9.8, J(gem)=12.1 (P—CHb); 3.59 dd, 1H, J(P,CHa)=8.9, J(gem)=12.1 (P—CHa); 3.61 dd, 1H, J(3'b,2')=6.8, J(gem)=12.9 (H-3'b); 3.70 m, 1H (H-2'); 3.71 dd, 1H, J(3'a,2')=3.6, J(gem)=12.9 (H-3'a);4.11 dd, 1H, J(1'b,2')=5.0, J(gem)=10.7 (H-1'b); 4.14 dd, 1H, J(1'a,2')=4.6, J(gem)=10.7 (H-1'a); 5.36 s, 1H (H-5); $^{13}C$ NMR ($D_2O$+NaOD); 60.62 (C-3'); 65.58 (C-1'); 68.03 d, J(P,C)=149.4 (P—C); 76.63 (C-5); 79.89 d, J(P,C)=10.7 (C-2'); 162.63 and 166.54 (C-2, C-4); 170.78 (C-6).

(b) 2,4-Diamino-6-[(S)-3-hydroxy-2-(phosphonomethoxy)propoxy]pyrimidine (S)-2,2-Dimethyl-4-hydroxymethyl-1,3-dioxolane (40 g, 0.3 mol) freshly prepared from 1,2:5,6-diisopropylidene-D-mannitol and distilled in vacuo and was added dropwise into a suspension of NaH (0.3 mol) in tetrahydrofuran (600 mL). The mixture was stirred 30 min and 2,4-diamino-6-chloropyrimidine (36.2 g, 0.25 mol) was added. The reaction mixture was refluxed under stirring in an argon atmosphere for 12 h and neutralized with acetic acid. The slurry was filtered, washed with tetrahydrofuran and the filtrate evaporated to dryness in vacuo. Purification on a silica gel column (600 mL) in chloroform gave, after crystallization from ethyl acetate—petroleum ether, 2,4-diamino-6-(S)-(2,2-dimethyl-1,3-dioxolan-4-ylmethoxy)pyrimidine. Yield, 46.0 g (76.6%). This compound (43.3 g, 0.18 mol) in 0.25 M $H_2SO_4$ (800 mL) was left to stand overnight at room temperature. The mixture was neutralized by saturated barium hydroxide solution, filtered, and the filtrate evaporated to dryness. The residue gave on recrystallization from 90% ethanol (ether added to turbidity) 2,4-diamino-6-(S)-(2,3-dihydroxypropoxy)pyrimidine, m.p. 149° C. Yield, 32.0 g (89%). For $C_7H_{12}N_4O_3$ (200.2) calculated 42.00% C, 6.04% H, 27.99% N; found 41.94% C, 6.35% H, 27.75% N. Mass spectrum: 201.2 ($MH^+$). NMR spectra were identical with those of the racemic compound.

The mixture of this compound (32.0 g, 0.16 mmol), trityl chloride (140 g, 0.5 mol) and 4-dimethylaminopyridine (3 g) in pyridine (500 mL) was stirred 24 h at 80° C. and poured slowly under stirring to water (5 L). The slurry was stirred for 1 h, decanted, and, after stirring with fresh portion of water (2L) it was filtered and washed with water. The precipitate was taken up in chloroform (2 L), dried with $MgSO_4$, evaporated and codistilled with toluene (3×200 mL portions) in vacuo. The resulting gum was dissolved in minimum volume of ether and dropped, under vigorous stirring, to petroleum ether (2.5 L). The precipitate was filtered, washed with petroleum ether and air-dried overnight. Drying in vacuo gave 99.5 g (69%) of 6-(S)-[2-hydroxy-3-(trityloxy)propoxy]-2,4-bis(tritylamino) pyrimidine. For $C_{64}H_{54}N_4O_2$ (911.1) calculated 6.15% N; found 5.96% N. This trityl derivative (99.5 g, 0.11 mol) and diisopropyl p-toluenesulfonyloxymethylphosphonate (42 g, 0.12 mol) in freshly dried tetrahydrofuran (600 mL) was treated with 60% NaH (14.4 g, 0.36 mol). The mixture was stirred at ambient temperature for 3 days, filtered over celite pad and the filtrate was treated with ethanol (20 mL). The solvent was stripped off in vacuo, the residue refluxed in 80% aqueous acetic acid (500 mL) for 30 min, and left to stand overnight at room temperature. The crystalline product was filtered, washed with 80% acetic acid and the filtrate was evaporated in vacuo. Water (700 mL) was added and the mixture was extracted with ether (4×200 mL). The aqueous phase was concentrated in vacuo and applied on a Dowex 50×8 column (250 mL) in acidic form. The column was washed with 20% aqueous methanol till the drop of acidity and UV-absorbance and then eluted with 2.5% ammonia in 20% aqueous methanol. The UV-absorbing ammonia eluate was collected, evaporated to dryness in vacuo, the residue codistilled with ethanol (3×100 mL) and dried over $P_2O_5$ in vacuo overnight. Acetonitrile (200 mL) and bromotrimethylsilane (50 mL) were added and the mixture was left to stand overnight under exclusion of moisture. After evaporation of the volatiles in vacuo, water (300 mL) was added to the residue followed by conc. aqueous ammonia to alkaline reaction. This solution was evaporated to dryness and the residue deionized on a Dowex 50×8 column (250 mL) under identical conditions. The UV-absorbing ammonia eluate was taken down in vacuo, the residue was dissolved in minimum amount of water and alkalized to pH 10 by ammonia. This solution was applied on a column (250 mL)

Dowex 1×2 (acetate form) prewashed with water. The column was washed with water till the drop of UV-absorbance of the eluate and then with linear gradient of acetic acid (0–0,3 M, 2 L each). The main UV-absorbing fraction was evaporated in vacuo and the residue was codistilled with water (2×100 mL). Recrystallization from water gave 2,4-diamino-6-(S)-[3-hydroxy-2-(phosphonomethoxy)propoxy]-pyrimidine as a monohydrate. Yield, 13.8 g (40%), white needles, m.p. For $C_8H_{15}N_4O_6P \cdot H_2O$ (312.2) calculated 30.78% C, 5.49% H, 17.94% N, 9.92% P; found 31.00% C, 5.70% H, 17.79% N, 9.75% P. Mass spectrum: 295.0 (MH$^+$). NMR spectra were identical with those of the racemic compound.

EXAMPLE 13

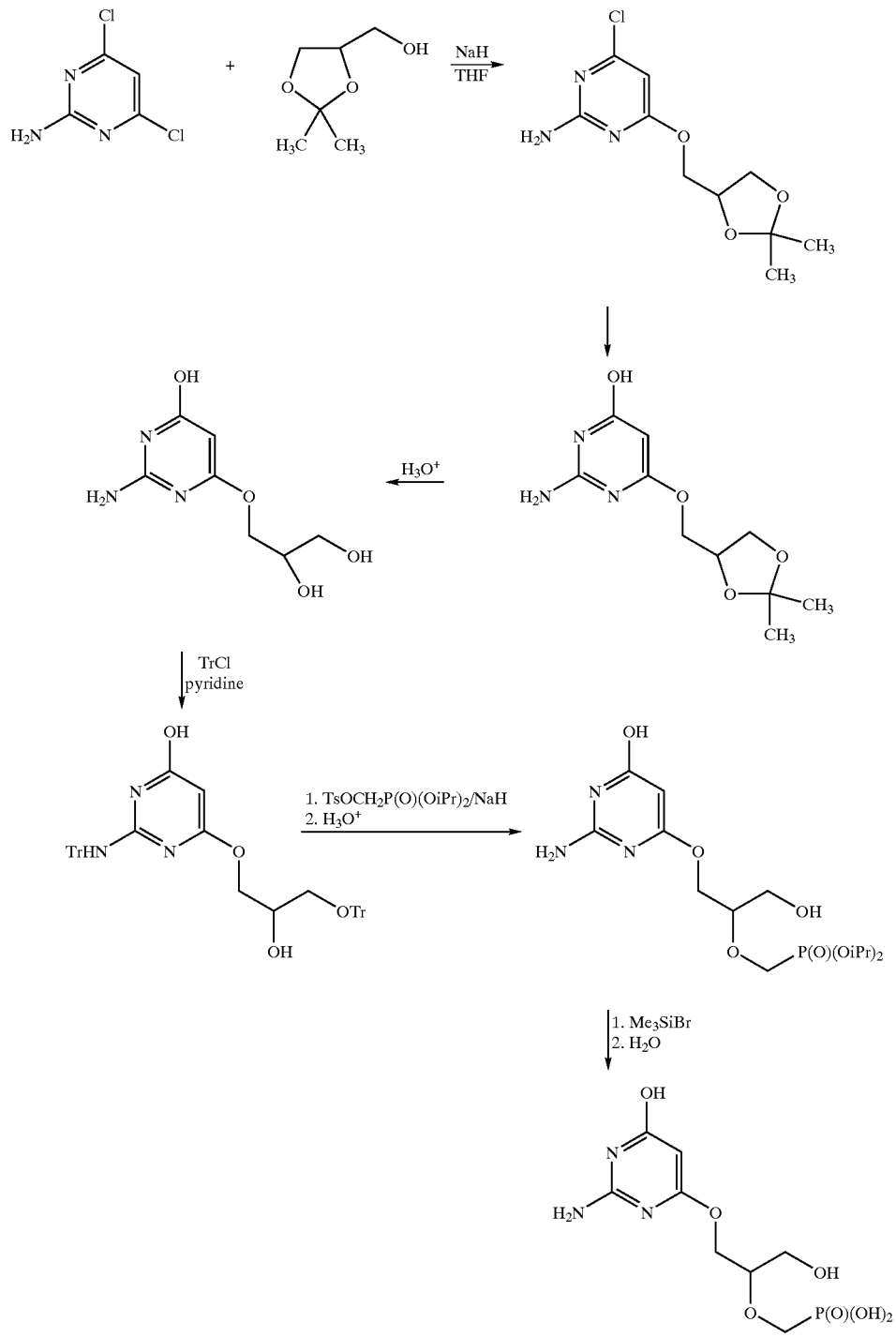

Tr ... $(C_6H_5)_3C$
Ts ... p-toluenesulfonyl
iPr ... isopopyl

2-Amino-4-hydroxy-6-[2(phosphonomethoxy)ethoxy]pyrimidine

4-Hydroxymethyl-2,2-dimethyl-1,3-dioxolane (15 mL, 0.12 mol) was added dropwise over 30 min to a stirred suspension of NaH (60% dispersion in paraffin oil, 4.8 g, 0.12 mol) in tetrahydrofuran (250 mL). After 1 h stirring at room temperature, 2-amino-4,6-dichloropyrimidine (16.4 g, 0.1 mol) was added and the mixture kept at reflux temperature, until the starting material essentially disappeared (TLC on silica gel plates; system methanol-chloroform, 1:9). The mixture was cooled, neutralized by addition of acetic acid, filtered over celite, washed with tetrahydrofuran and evaporated in vacuo. The residue was decanted twice with ether (100 mL each), dissolved in chloroform (100 mL) and filtered through a short silica gel column (washing with 1 L chloroform). The filtrate was evaporated in vacuo and the residue was dissolved in hot ethyl acetate; an equal volume of ether was cautiously added to the warm solution, followed by petroleum ether till turbidity. The product which crystallized in a refrigerator, was collected by filtration, washed with ether/petroleum ether mixture (1:1) and dried in vacuo. Yield, 20.5 g (79%) of 2-amino-4-chloro-6-[2,2-dimethyl-1,3-dioxolan-4-ylmethoxy]pyrimidine, m.p. 152° C. For $C_{10}H_{14}ClN_3O_3$ (259.7) calculated 46.25% C, 5.43% H, 13.65% Cl, 16.18% N; found 46.45% C, 5.46% H, 13.90% Cl, 15.95% N. $^1$H NMR (CD$_3$SOCD$_3$): 1.28 s, 3H and 1.33 s, 3H (CH$_3$); 3.71 dd, 1H, J(3'b,2')=6.1, J(gem)=8.4 (H-3'b); 4.05 dd, 1H, J(3'a,2')=6.6, J(gem)=8.4 (H-3'a); 4.22 dd, 1H, J(1'b,2')=6.3, J(gem)=11.2 (H-1'b); 4.28 dd, 1H, J(1'a,2')=4.5, J(gem)=11.2 (H-1'a); 4.35 m, 1H (H-2'); 6.10 s, 1H (H-5); 7.08 br s, 2H (NH$_2$). $^{13}$C NMR (CD$_3$SOCD$_3$): 25.48 and 26.76 (CH$_3$); 65.82 and 66.84 (C-1', C-3'); 73.35 (C-2'); 94.48 (C-5); 109.05 (C$_{iPr}$); 160.21 (C-2); 162.95 (C-4); 170.48 (C-6).

The mixture of this compound (13 g, 50 mmol), DABCO (12 g) and K$_2$CO$_3$ (21.5 g) in water (300 mL) was stirred 3 hours at reflux temperature. After cooling to the room temperature, Dowex 50×8 (acid form) was added portion wise under stirring to pH~6, to decompose the carbonate and neutralize DABCO. The suspension was then slightly alkalized by adding conc. aqueous ammonia, filtered, washed with water and the filtrate was evaporated in vacuo. The resin was resuspended in diluted (1:20) aqueous ammonia (300 mL), filtered and the resin subsequently washed with boiling water (4×200 mL). The filtrate and washings were evaporated in vacuo. The both residues were dried by codistillation with ethanol and extracted with chloroform. The semicrystalline solid was filtered, washed with chloroform and adsorbed from methanolic solution on silica gel (50 mL). This material was applied on a short column (150 mL) in chloroform and the product was eluted with chloroform-methanol mixture (9:1). Crystallization from ethanol (ether added to turbidity) gave 2-amino-4-hydroxy-6-[(2,2-dimethyl-1,3-dioxolan-4-yl)methoxy]pyrimidine, m.p. 258° C. Yield, 8.2 g (68%). For $C_{10}H_{15}N_3O_4$ (241.2) calculated 46.25% C, 5.43% H, 13.65% Cl, 16.18% N; found 46.45% C, 5.46% H, 13.90% Cl, 15.95% N. Mass spectrum: 242 (M+H). $^1$H NMR (CD$_3$SOCD$_3$): 1.27 s, 3H and 1.32 s, 3H (CH$_3$); 3.67 dd, 1H, J(3'b,2')=6.2, J(gem)=8.4 (H-3'b); 4.02 dd, 1H, J(3'a,2')=6.6, J(gem)=8.4 (H-3'a); 4.05 dd, 1H, J(1'b,2')=6.1, J(gem)=11.0 (H-1'b); 4.10 dd, 1H, J(1'a,2')=4.6, J(gem)=11.0 (H-1'a); 4.30 qd, 1H, J(1'a,2')=4.6, J(2',1')–J(2',3')=6.3 (H-2'); 4.78 s, 1H (H-5); 6.67 br s, 2H (NH$_2$), 10.47 br s, 1H (NH). $^{13}$C NMR (CD$_3$SOCD$_3$): 25.54 and 26.78 (CH$_3$) 65.83 (C-3'); 66.70 (C-1',); 73.63 (C-2'); 79.99 (C-5); 108.94 (C$_{iPr}$); 164.25 and 155.69 (C-2, C-6).

EXAMPLE 14

2-Amino-6-[2-(diisopropylphosphonylmethoxy)ethoxy]-4-hydroxypyrimidine

A mixture of 2-amino-4-chloro-6-[2-(diisopropylphosphonylmethoxy)ethoxy]pyrimidine (5.7 g), DABCO (3.6 g) and K$_2$CO$_3$ (9.0 g) in water (100 mL) was refluxed 150 min under stirring, cooled and acidified by addition of Dowex 50×8 (H$^+$-form). The suspension was alkalified with conc. aqueous ammonia and, after 5 min stirring, filtered and the resin washed with 50% aqueous methanol (200 mL). The filtrate was evaporated to dryness, ethanol (50 mL) was added and the mixture evaporated to dryness. The residue gave on chromatography on silica gel column (150 mL) with chloroform-ethanol gradient crystalline 2-amino-6-[2-(diisopropylphosphonylmethoxy)ethoxy]-4-hydroxypyrimidine, m.p.154° C. in 78% yield. For $C_{13}H_{24}N_3O_6P$ (349.3) calculated 44.70% C, 6.92% H, 12.03% N, 8.37% P; found 44.58% C, 7.02% H, 11.95% N, 8.53% P. $^1$H NMR (CD$_3$SOCD$_3$): 1.24 d, 6H and 1.23 d, 6H, J(CH$_3$,CH)=6.2 (4×CH$_3$); 3.74 m, 2H (H-2'); 3.76 d, J(CH$_2$—P)=8.3 (CH$_2$—P); 4.19 m, 2H (H-1'); 4.59 m, 2H (P—OCH); 4.75 s, 1H (H-5); 6.65 bs, 2H, 2H (NH$_2$); 10.45 s, 1H (OH). $^{13}$C NMR (CD$_3$SOCD$_3$): 23.87 d, 2C, J(CH$_3$, P)=4.9 and 24.01 d, 2C, J(P,C)=3.9 (CH$_3$); 65.03 d, J(P,C)= 164.6 (P—C); 65.04 (C-1'); 70.37 d, 2C, J(P,C)=6.3) (P—OC); 70.87 d, J(P,C)=11.7 (C-2'); 79.95 (C-5); 155.68 (C-4); 164.25 (C-2); 171.01 (C-6).

This product was treated with bromotrimethylsilane (10 mL) in acetonitrile (80 mL) overnight, evaporated in vacuo and the residue treated with water (50 mL). After 10 min, conc. aqueous ammonia was added to alkaline reaction and the mixture evaporated. The residue was deionized on a column (100 mL) of Dowex 50×8 and the UV-absorbing ammonia eluate was evaporated to dryness. It was dissolved in minimum hot water by addition of conc. aqueous ammonia and acidified by conc. HCl to pH 3–3.5. The precipitate was collected, washed with water, ethanol and dried in vacuo, to afford 2-amino-6-[2-(diisopropylphosphonylmethoxy)ethoxy]-4-hydroxypyrimidine. Yield, 0.7 g, m.p. 227° C. For $C_7H_{12}N_3O_6P$ (265.16) calculated 31.71% C, 4.56% H, 15.85% N, 11.68% P; found 31.55% C, 4.62% H, 16.15% N, 11.51% P.

EXAMPLE 15

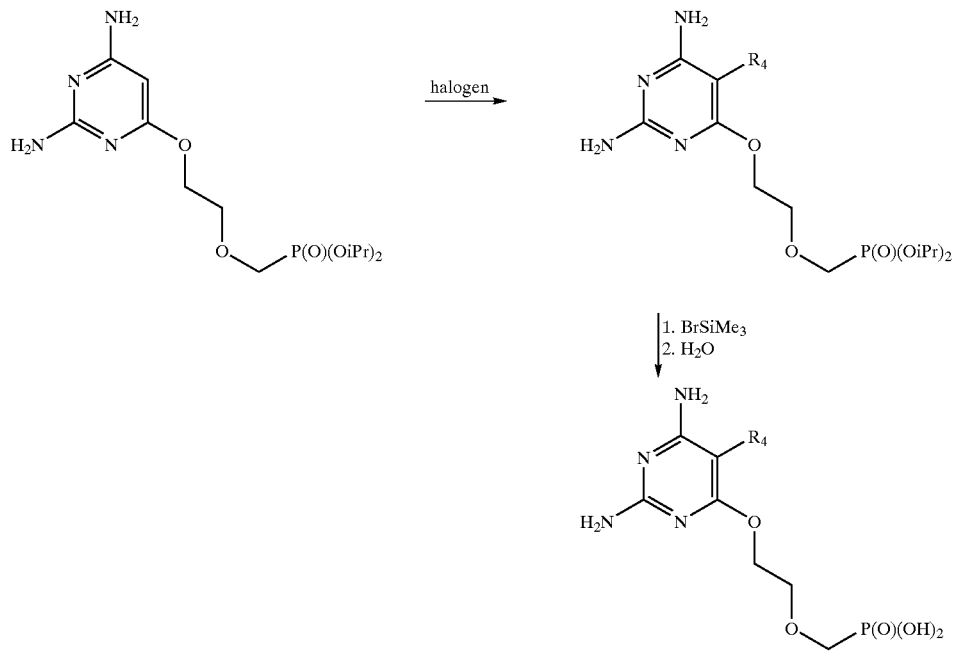

R₄ = halogen 2,4-Diamino-5-bromo-6-[2-(phosphonomethoxy) ethoxy]pyrimidine 2,4-Diamino-6-[2-(diisopropylphosphonylmethoxy) ethoxy]pyrimidine (4.3 g, 12.3 mmol) in DMF (40 mL) was stirred with bromine solution in $CCl_4$ (0.3 M, 50 mL) for 3 h at ambient temperature, alkalified with triethylamine and evaporated. The crude product was purified on silica gel column (150 mL) in the system chloroform—ethanol and crystallized from ethyl acetate—petroleum ether. Yield, 3.9 g (11.9 mmol) of the diester which was treated with bromotrimethylsilane (20 mL) in acetonitrile (50 mL) overnight, evaporated in vacuo and decomposed by ammonia-water. After deionisation on Dowex 50 (100 mL column), the residue of the ammonia eluate was purified by Dowex 1×2 column (100 mL) chromatography with a gradient of acetic acid (0–0,5 M, 1 L each). The main fraction was evaporated and crystallized from water to afford 3.1 g (84%) of the title compound, m.p.218° C. For $C_7H_{12}BrN_4O_5P$ (343.07) calculated 24.51% C, 3.53% H, 23.29% Br, 16.33% N, 9.03% P; found 24.56% C, 3.55% H, 23.51% Br, 16.07% N, 8.89% P.

This reaction is repeated with 2-amino-6-[2-diisopropylphosphonylmethoxy)ethoxy]-4-hydroxypyrimidine to afford the 5-halogeno analogue.

EXAMPLE 16

The antiviral activities of compounds herein were determined in accord with the general procedures disclosed in J. Balzarini, et al. "9-(2-phosphonylmethoxyethyl)adenine (PMEA) effectively inhibits retrovirus replication in vitro and simian immunodeficiency virus infection in rhesus monkeys" *AIDS* 5:21–28, 1991 and J. Balzarini, et al. "Differential antiherpesvirus and antiretrovirus effects of the (S) and (R) enantiomers of acyclic nucleoside phosphonates: potent and selective in vitro and in vivo antiretrovirus activities of (R)-9-(2-phosphonomethoxypropyl)-2,6-diaminopurine" *Antimicrobial Agents and Chemotherapy*, 37:332–338, 1993.

The results are shown in Table 1a, where greater potency is indicated by lower absolute values.

EXAMPLE 17

Viruses. The origins of MSV, HIV type 1 (HIV-1) (strain III$_B$ and Ba-L), HIV-2 (strain ROD) and FIV (strain Petaluma) have been described previously (Balzarini et al., AIDS 5: 21–28, 1991; De Clercq et al., Proc. Soc. Exp. Biol. Med. 137:590–594, 1971; Egberink et al., Proc. Natl. Acad. Sci. 87:3087–3091, 1990; Hartmann et al., Antiviral Chem. Chemother. 5:13–19, 1994; Popovic et al., Science 224:497–500, 1984). HIV-1(III$_B$) and HIV-2(ROD) stocks were obtained from supernatants of virus-infected MT-4 cell cultures. HIV-1$_{BaL}$ was expanded in human primary M/M, whose supernatants were collected, filtered and stored at −80° C. before use. Characteristics of viral stocks used for this study were 2.1×10⁸ HIV-RNA genomes/ml (corresponding to 35 ng of p24 antigen) and 5,000 tissue culture infectious doses 50% per ml (TCID$_{50}$/ml) as assessed by virus titration in other primary M/M cultures. The isolation and characterization of the clinical HIV-1 isolates L1S, L6S and L6S/PMEA has been reported (Thormar et al., Proc. Natl. Acad. Sci. USA 93:3283–3287, 1995; Van Laethem et al., AIDS 15:553–561, 2001). The HIV-1/L1S clinical isolate was derived from a patient not treated with NRTIs (nucleoside reverse transcriptase inhibitors) or ANPs and cultured without the selective pressure of any drugs. Therefore, it contained no obvious mutations that are characteristic for NRTI- or ANP-treated patients. HIV-1/L6S is a clinical isolate from a drug-treated individual cultured without the selective pressure of any drugs. As is characteristic for NRTI-treated patients, it contained S68G, K70T, V75I, F77L, F116Y and Q151M mutations in its RT. HIV-1/L6S/PMEA is the clinical isolate HIV-1/L6S that has been isolated after culturing the virus for 11 passages in the presence of increasing concentrations of PMEA (adefovir). It gained, in addition to the mutations mentioned for HIV-1/L6S, also the PMEA-characteristic K65R mutation in its reverse transcriptase (RT).

Radiochemicals. [Methyl-$^3$H]thymidine (specific radioactivity 42 Ci/mmole), [5-$^3$H]uridine (specific radioactivity: 26 Ci/mmole) and [4,5-$^3$H]leucine (specific radioactivity: 52 Ci/mmole) were derived from Amersham Pharmacia Biotech (Buckinghamshire, U.K.).

Compounds. Following compounds were used in this study: 1,2,4-diamino-6-[2-(phosphonomethoxy)ethoxy] pyrimidine; 2,2,4-diamino-6-{[2-(phosphonomethoxy) ethyl]-sulfanyl}pyrimidine; 3,4-amino-6-[2-(phosphonomethoxy)ethoxy]pyrimidine; 4,2-amino-4-hydroxy-6-[2-(phosphonomethoxy)ethoxy]pyrimidine; 5,2-amino-4-hydroxy-6-{[2-(phosphono-methoxy)ethyl] sulfanyl}pyrimidine; 6,2-amino-4-dimethylamino-6-[2-(phosphonomethoxy)-ethoxy]pyrimidine; 7,2-amino-4-cyclopropylamino-6-[2-(phosphonomethoxy)ethoxy] pyrimidine; 8,4-amino-2-methylsulfanyl-6-[2-(phosphonomethoxy)ethoxy]pyrimidine; 9,2-amino-4-methyl-6-[2-(phosphonomethoxy)ethoxy]pyrimidine; 10,2, 4-diamino-6-(S)-[2-(phosphonomethoxy)propoxy] pyrimidine; 11,2,4-diamino-6-(R)-[2-(phosphonomethoxy) propoxy]pyrimidine; PMEA, 9-[(2-phosphonomethoxy) ethyl]adenine; (R)-PMPA, (R)-9-[(2-phosphonomethoxy)-propyl]adenine.

In vitro antiviral assays. The activity against HIV-1- and HIV-2-induced cytopathicity was examined in MT-4 cell cultures at day 5 post infection and based on the determination of cell viability by trypan blue dye staining or in CEM cell cultures at day 4 to 5 post infection and based on the microscopical examination of virus-induced giant cell formation. HIV-1 and HIV-2 were added at 100 CCID$_{50}$ to the cell cultures.

Peripheral blood mononuclear cells (PBMC) from healthy donors were isolated by density centrifugation (Lymphoprep; Nycomed Pharma, AS Diagnostics, Oslo, Norway) and stimulated with phytohemagglutin (PHA) (Sigma Chemical Co., Bornem, Belgium) for 3 days. The activated cells (PHA-stimulated blasts) were washed with PBS and viral infections were done as described by the AIDS clinical trial group protocols. Briefly, PBMCs ($2\times10^5$/ 200 well) were plated in the presence of serial dilutions of the test compound and were infected with HIV stocks at 1000 CCID$_{50}$ per mL. At day 4 post-infection, 125 µl of the supernatant of the infected cultures was removed and replaced with 150 µl of fresh medium containing the test compounds at the appropriate concentrations. At 7 days after plating the cells, p24 antigen was detected in the culture supernatant by an enzyme-linked immunosorbent assay (NEN, Paris, France).

Human primary macrophages (M/M) were prepared and purified as follows. Peripheral blood mononuclear cells (PBMC), obtained from healthy HIV-1-negative donors were separated over a Ficoll gradient and seeded in 48-well plates at $1.8\times10^6$ cells/well in 1 ml of RPMI 1640 containing 20% heat-inactivated, endotoxin- and mycoplasma-free fetal bovine serum (Hyclone Laboratories, Inc., Logan, Utah), 4 mM L-glutamine (Life Technologies), 50 U/ml penicillin and 50 µl g/ml streptomycin (Life Technologies) (hereinafter referred to as complete medium). Five days after plating and culturing the PBMC at 37° C. in a humidified atmosphere enriched with 5% CO$_2$-adherent cells were carefully removed with repeated washings with warmed RPMI-1640, leaving a monolayer of adherent cells which were finally incubated in complete medium. Cells treated under these conditions have previously been shown to be >97% M/M, as determined by cytofluorimetric analysis. Macrophages were treated for 30 minutes with the compounds, then challenged with 300 TCID$_{50}$/ml of HIV-1$_{BaL}$. Two hours after virus challenge, M/M were washed to remove the viral inoculum, complete medium containing the appropriate compound concentrations was replaced where requested, and the M/M were then cultured for the duration of the experiments. Each compound concentration was run in triplicate while positive controls were run in sextuplicate. Therefore, compounds were replaced each time of medium change. Supernatants were collected at day 14 after infection for assessment of virus production by analysis of HIV-1-p24 antigen.

For the anti-FIV assays, $10^5$ CrFK cells were seeded onto 24-well tissue culture plates. Cells were cultured with 2 ml of culture medium/well containing 2.5% of fetal calf serum in the presence of various drug concentrations. The assays were carried out in triplicate. After a 1-hr incubation period at 37° C., cells were infected with FIV. Virus was left in contact with the cultures for 1 day, after which the medium was removed and new medium containing the appropriate drug concentrations was added. After 6 days, the presence of FIV p24 antigen was examined by an antigen capture assay.

The inhibitory effect of the test compounds on MSV-induced transformation of murine embryo fibroblast C3H/ 3T3 cell cultures was examined microscopically at day 6 post infection. MSV was added at 75 focus-forming units to the cell cultures. The detailed procedures for the antiretroviral evaluations has been described in detail before (Balzarini et al., AIDS 5:21–28, 1991; Balzarini et al., Antimicrob. Agents Chemother. 37:332–338, 1993; De Clercq et al., Proc. Soc. Exp. Biol. Med. 137:590–594, 1971).

Anti-MSV activity in vivo. The inhibitory effects of the compounds on the initiation of MSV-induced tumor formation and survival of MSV-inoculated mice were evaluated as previously described (Balzarini et al., Proc. Natl. Acad. Sci. USA 86:332–336, 1989; Balzarini et al., Proc. Natl. Acad. Sci. USA 88:4961–4965, 1991; Balzarini et al., Antimicrob. Agents Chemother. 37:332–338, 1993). Briefly, 2- to 3-day-old NMRI mice were each inoculated subcutaneously in the left hind leg with MSV and treated intraperitoneally with a single dose of test compound at 4 h prior to virus infection (day 1) followed by a single dose of test compound at days 2, 3, 4 and 5. Drug doses were 50, 20, 8, 4 and/or 2 mg/kg/day for tenofovir [(R)-PMPA], adefovir (PMEA), 1 (designated PMEO-2,4-di-NH$_2$-Pym), 2 (designated PMES-2,4-di-NH$_2$-Pym) and 11 (designated (R)-PMPO-2,4-di-NH$_2$-Pym). No toxicity was observed for the highest dose of the test compound. The appearance and growth of MSV-induced tumors at the site of virus inoculation, as well as survival of the mice for up to 30 days post infection, were recorded daily.

Cytostatic and antimetabolic effect of acyclic nucleoside phosphonates in vitro. The assays to examine the inhibition of CEM cell growth by the test compounds have been described previously (Balzarini et al., AIDS 5:21–28, 1991). The 50% cytostatic concentration (CC$_{50}$) was defined as the concentration of compound that reduced the number of living cells by 50%. To measure MT-4 cell toxicity of the test compounds, $5\times10^4$ MT-4 cells were incubated in the wells of 96-well microplates in the presence or absence of different concentrations of the test compounds for 5 days at 37° C. The CC$_{50}$ was then calculated from the number of living cells counted under a microscope by the trypan blue exclusion method.

The incorporation of [methyl-$^3$H]thymidine, [$^3$H]uridine and [$^3$H]leucine into the methanol-insoluble CEM cell fraction was also measured in microplates. To each well were added $10^5$ CEM cells, 5.9 pmol (0.25 µCi) of [methyl-$^3$H] thymidine, 38 pmol (1.0 µCi) of [$^3$H]uridine and 19 pmol (1.0 µCi) [4,5-$^3$H]leucine, and a given amount of the test compound. The cells were allowed to proliferate for 20 h at 37° C. in a humidified, $CO_2$-controlled atmosphere. At the end of this incubation period, the contents of the wells (200 μl) were brought onto 25-mm glass fiber filters (type A/G; Gelman Instrument Co., Ann Arbor, Mich.) mounted on a Millipore 3025 sampling manifold apparatus. The filters were washed twice with cold PBS (phosphate-buffered saline), twice with cold 10% trichloroacetic acid, twice with cold 5% trichloroacetic acid, once with cold ethanol, and once with cold ether. The filters were then allowed to dry for 10 min at 60° C. and assayed for radioactivity in a toluene-based scintillant.

Anti-HIV-1 activity of acyclic pyrimidine nucleoside phosphonate analogues in CEM cell cultures. A prerequisite for potent antiretroviral activity is the presence of an amino group at C-2 of the pyrimidine ring together with an amino group at C-4 (i.e.compounds 1, 2, 11) or a hydroxyl group at C-4 (i.e. compound 4) (Table 1). These 6-PMEO and 6-PMPO substituted pyrimidine structures resulted in an anti-HIV activity with an $EC_{50}$ that ranked between 0.80 and 2.0 μg/ml. Lack of an amino group at C-2 (i.e. compound 3 or 8), or the presence of a dimethylamino or methyl or cyclopropylamino at C-4 (i.e. compounds 6, 9 and 7, respectively) resulted in complete annihilation of the anti-retroviral activity (Table 1). Thioether derivatives were, as a rule, 5- to 10-fold less active than the corresponding ether derivatives (i.e. compare compound 2 with compound 1), or even completely inactive (i.e. compound 5). Interestingly, the antiretroviral activity of the novel pyrimidine ANPs showed marked enantiospecificity in their action against HIV-1. The (R)-6-PMPO pyrimidine derivative 11 was markedly more inhibitory to these viruses than the corresponding (S)-6-PMPO pyrimidine derivative (10) (Table 1). The residual antiviral activity noted for the (S)-enantiomer might be due to the contamination with (R)-enantiomer originating from the chiral starting material (1–2%).

For most of the compounds, poor, if any cytotoxicity was noted at a concentration of 100 μg/mL, with a striking exception for compound 4 ($CC_{50}$: 2.5 μg/mL for CEM cells). The antivirally most active 6-PMEO-2,4-di-$NH_2$ pyrimidine derivative (compound 1) showed a $CC_{50}$ of 11 μg/mL for CEM cells, whereas its corresponding thioether analogue 2 and the (R)-6-PMPO-2,4-di-$NH_2$ pyrimidine derivative 11 had $CC_{50}$ values around 60 μg/ml (Table 1). Interestingly, the 5-bromo-derivative of 1 was active against HIV-1 in CEM cell cultures at 2.5 μg/mL, and not toxic at 100 μg/mL. Neither compounds 1 nor 2, nor compound 11 were inhibitory towards [$^3$H]dThd, [$^3$H]Urd and [$^3$H]leu incorporation into TCA-insoluble CEM cell material within a 12 hour incubation period at 200 μg/mL. Also, PMEA and (R)-PMPA were not inhibitory to macromolecular synthesis at this drug concentration (data not shown).

Anti-retrovirus activity of acyclic pyrimidine nucleoside phosphonate analogues in several virus/cell systems. The 6-PMEO derivatives 1 and 4, the 6-PME thioether (6-PMES) 2, and the (R)-6-PMPO derivative 11 were evaluated for their inhibitory activity against several in vitro retrovirus models (Table 2). As a rule, the antiviral activity values of the test compounds found for HIV-1($III_B$) in CEM cell cultures (Table 1) matched very closely the antiviral activity values found for HIV-2(ROD) in CEM cells, HIV-1 and HIV-2 in MT-4 cell cultures, and FIV in feline Crandell kidney cells. Thus, the $EC_{50}$ values of compound 1 for HIV ranged between 0.29 and 0.80 μg/mL, and for compound 11 between 1.3 and 3.0 μg/mL. These values were close to those observed for the reference compounds PMEA (adefovir) ($EC_{50}$: 0.96–2.0 μg/mL) and (R)-PMPA (tenofovir) ($EC_{50}$: 0.36–0.52 μg/mL). When the 6-PMEO and 6-(R)-PMPO derivatives were evaluated against HIV-1 in primary cells [HIV-1($III_B$) in PBL and HIV-1(Ba-L) in monocyte/macrophages (M/M)], the antiretroviral potency was even more pronounced. Indeed, compounds 1 and 11 inhibited the virus in PBL at an $EC_{50}$ of 0.07 and 0.12 μg/mL, respectively, compared with 1.9 and 0.33 μg/mL for the reference compounds PMEA and (R)-PMPA. The 6-PMEO and (R)-6-PMPO derivatives were even more inhibitory to HIV-1 (Ba-L) in M/M, as also observed for PMEA and (R)-PMPA. As a rule, the compounds proved less cytotoxic in MT-4, as compared to CEM cells, and not toxic at 100 μg/mL in monocyte/macrophages.

Since it has been previously shown that PMEA and (R)-PMPA exhibit pronounced inhibitory activity against murine Moloney sarcoma virus (MSV) in both cell culture and newborn mice, the novel 6-PMEO and (R)-6-PMPO derivatives were also evaluated for their in vitro activity against MSV. Compounds 1, 11 and 4 were highly inhibitory against MSV-induced C3H cell transformation. The $EC_{50}$ values were as low as 0.05–0.15 μg/mL (Table 2).

Effect of natural nucleosides and nucleobases on the anti-HIV activity of the acyclic pyrimidine nucleoside phosphonate analogues in cell culture. It is well known that the anti-HIV activity of pyrimidine nucleoside analogues such as 3'-azido-3'-deoxythymidine (AZT, zidovudine) and 2',3'-dideoxycytidine (ddC, zalcitabine) can be affected (i.e. diminished) in the presence of natural nucleosides such as dThd and dCyd (Balzarini et al., Textbook of AIDS Medicine, chapter 49, Broder, S., T. C. Merigan, and D. Bolognesi, eds. Williams & Wilkins, Baltimore, Md., pp. 751–772, 1994; Balzarini et al., Antimicrob. Agents Chemother. 37:332–338, 1993). Therefore, to estimate whether the presence of natural nucleosides and nucleobases could influence the anti-HIV activity of the novel 6-PMEO and (R)-6-PMPO pyrimidine derivatives, the effect of subtoxic concentrations of the pyrimidine nucleosides thymidine (dThd) and 2'-deoxycytidine (dCyd), the purine nucleosides adenosine (Ado) and guanosine (Guo), and the nucleobase adenine (Ade), were examined (Table 3). None of the natural nucleosides and nucleobases had any measurable influence on the anti-HIV-1 activity of the test compounds in CEM cell cultures. In all cases, the antiretroviral activity of the compounds was fully preserved, as was also the case for the reference compounds PMEA, (R)-PMPA and PMEG (Table 3).

Efficacy of acyclic pyrimidine nucleoside phosphonate analogues against MSV-induced tumor formation in newborn NMRI mice. The 6-PMEO derivative 1 and its thioether analogue 2, and the (R)-6-PMPO derivative 11 were evaluated for their inhibitory effect on MSV-induced tumor formation and associated death in newborn NMRI mice (Table 4). PMEA (adefovir) and (R)-PMPA (tenofovir) were included as reference compounds. Of the novel 6-PMEO and (R)-6-PMPO derivatives, compound 1 proved to be most efficient in preventing MSV-induced tumor formation and associated death of newborn NMRI mice (Table 4). At least 80% of mice were protected from tumor formation at 50 and 20 mg/kg, and the remaining mice that developed tumors survived for more than 30 days post infection. At a dose as low as 2 mg/kg, compound 1 could still prevent tumor formation in 5% of the mice and afforded 15% long-term survivors. Compound 1 had a comparable ability to prevent tumor formation and associated animal death as PMEA and (R)-PMPA (Table 4). In contrast, the corresponding thioether derivative 2 was unable to prevent tumor formation at all doses tested, and it afforded 20% long-term survivors at a dose of 8–50 mg/kg. The capacity of the (R)-6-PMPO derivative 11 to prevent tumor formation and associated death was intermediate between that observed for compounds 1 and 2. All drugs delayed MSV-induced tumor formation in a dose-dependent manner. Compound 1 had an inhibitory effect that was comparable with that of (R)-PMPA and PMEA. Compound 11 was inferior to compound 1, and compound 2 only showed a pronounced delay in tumor formation at a dose of 50 mg/kg. As noted for tumor formation, delay of associated animal death was also afforded in a dose-dependent manner, and compound 1 was at least as efficient in delaying death as the reference drugs PMEA and (R)-PMPA.

Sensitivity of mutated HIV-1 strains towards acyclic pyrimidine nucleoside phosphonate analogues in CEM cell cultures. Compounds 1, 2 and 11 were evaluated for their inhibitory activity against HIV-1(III$_B$) strains containing the nonnucleoside RT inhibitor (NNRTI)-specific L100I, K103N, Y181C and Y188H mutations in the RT. All three compounds retained full activity against these mutant virus strains (data not shown). The same compounds were also evaluated on their inhibitory effect on the clinical isolates HIV-1/L1S, HIV-1/L6S and HIV-1/L6S/PMEA (Table 5). PMEA and (R)-PMPA were included as reference compounds. Compound 1 retained pronounced antiviral activity against the three virus strains. Compounds 2 and particularly 11 showed clearly decreased activity against the HIV-1/L6S/PMEA isolate and so did PMEA and (R)-PMPA. Thus, the multi-NRTI resistance mutations (S68G, K70T, V75I, F77L, F116Y and Q151M) and the PMEA-characteristic K65R mutation present in HIV-1/L6S/PMEA did not markedly affect the antiviral potency of compound 1 and PMEA (~3.6- to 4.5-fold increased EC$_{50}$) while more extensively decreasing sensitivity to the other ANPs (Table 5).

TABLE 1a

Antiviral Activity (EC$_{50}$ μg/mL)

| Code | HSV-1 (KOS) | HSV-2 (G) | HSV-1 TK- VMW 1837 | CMV AD-169 | CMV Davis | VZV TK+ OKA | VZV TK+ YS | VZV TK- 07/1 | VZV TK- YS/R | MSV | HIV-1 | HIV-2 |
|---|---|---|---|---|---|---|---|---|---|---|---|---|
| H-3404 | 6.5 | 24 | 9.6 | >50 | >50 | 1.2 | 1.1 | 2.5 | 1.6 | 0.035 ± 0.002 | 0.8 ± 0 | 0.43 ± 0.32 |
| H-3408 | 29 | ≧80 | 48 | >50 | >50 | 7.5 | 7 | 20 | 15 | 1.70 | 5.5 ± 2.1 | 3.0 ± 1.4 |
| H-3415 | >80 | >80 | >80 | >50 | >50 | >50 | >50 | >50 | >50 | >40 | >100 | >100 |
| H-3418 | >16 | >16 | >16 | >50 | >50 | >50 | >50 | >50 | >50 | 12.6 ± 7.6 | >100 | >100 |
| H-3427 | >400 | >400 | >400 | >50 | >50 | >50 | >50 | >50 | >50 | 139 ± 11 | >100 | >100 |
| H-3435 | 240 | >80 | 240 | >50 | >50 | >20 | >50 | >50 | >50 | >40 | >100 | >100 |
| H-3444 | 240 | >400 | 240 | >50 | >50 | >50 | >50 | >50 | >50 | 4.26 ± 0.75 | 56.7 ± 37.9 | 80 ± 34.6 |
| H-3445 | >400 | >400 | >400 | >50 | >50 | >50 | >50 | >50 | >50 | 107 ± 10 | >100 | >100 |
| H-3453 | >400 | >400 | >400 | >50 | >50 | >50 | >50 | >50 | >50 | 89.4 ± 37.6 | >100 | >100 |
| H-3560 | >80 | >80 | >80 | >50 | >50 | >50 | >50 | >50 | >50 | 6.1 | 51 | 33 |
| H-3567 | 16 | 48 | 9.6 | >50 | >50 | 3.8 | 5.9 | 6.3 | 5.7 | 0.05 | 1.9 | 1.3 |
| H-3574 | 9.6 | 9.6 | 9.6 | 14 | 16 | 1.1 | 0.9 | | 0.6 | 0.08 | | >0.8 |

TABLE 1

Anti-retroviral and cytostatic activity of acyclic pyrimidine nucleoside phosphonates in HIV-1 infected CEM cell cultures

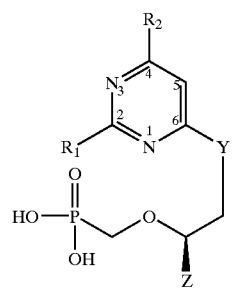

| Compound Code Number | Pyrimidine Analog of | R$_1$ | R$_2$ | Y | Z | EC$_{50}$[a] (μg/ml) HIV-1 (CEM) | CC$_{50}$[b] (μg/ml) (CEM |
|---|---|---|---|---|---|---|---|
| 1 | PMEDAP | NH$_2$ | NH$_2$ | O | H | 0.80 | 11 |
| 2 | PMEDAP | NH$_2$ | NH$_2$ | S | H | 5.5 | 64 |

TABLE 1-continued

Anti-retroviral and cytostatic activity of acyclic pyrimidine nucleoside phosphonates in HIV-1 infected CEM cell cultures

| Compound Code Number | Pyrimidine Analog of | $R_1$ | $R_2$ | Y | Z | $EC_{50}{}^a$ ($\mu$g/ml) HIV-1 (CEM) | $CC_{50}{}^b$ ($\mu$g/ml) (CEM) |
|---|---|---|---|---|---|---|---|
| 3 | PMEA | H | $NH_2$ | O | H | >100 | >100 |
| 4 | PMEG | $NH_2$ | OH | O | H | 2.2 | 2.5 |
| 5 | PMEG | $NH_2$ | OH | S | H | >100 | >100 |
| 6 | PMEDAP | $NH_2$ | $N(CH_3)_2$ | O | H | >100 | >100 |
| 7 | PMEDAP | $NH_2$ | NH-Cp$^c$ | O | H | >100 | >100 |
| 8 | PMEA | $SCH_3$ | $NH_2$ | O | H | >100 | >100 |
| 9 | PME-6-Me-MAP | $NH_2$ | $CH_2$ | O | H | >100 | >100 |
| 10 | (S)-PMPDAP | $NH_2$ | $NH_2$ | O | $CH_3$ | 51 | >100 |
| 11 | (R)-PMPDAP | $NH_2$ | $NH_2$ | O | $CH_3$ | 1.8 | 62 |
| Reference Drugs | | | | | | | |
| PMEA (adefovir) | | | | | | 0.96 | 16 |
| (R)-PMPA (tenofovir) | | | | | | 0.36 | 125 |

$^a$50% Effective concentration, or compound concentration required to inhibit HIV-1(III$_B$)-induced cytopathicity in CEM cell cultures by 50%.
$^b$50% Cytostatic concentration, or compound concentration required to inhibit CEM cell proliferation by 50%.
$^c$CP, cyclopropyl.

TABLE 2

Anti-retrovirus activity of 6-PMEO and (R)-6-PMPO derivatives in different cell types

| Cmpd Code No. | $EC_{50}{}^{a,d}$ ($\mu$g/ml) | | | | | | | |
|---|---|---|---|---|---|---|---|---|
| | HIV-1 (III$_B$) (CEM) | HIV-2 (ROD) (CEM) | HIV-1 (III$_B$) (MT-4) | HIV-2 (ROD) (MT-4) | HIV-1 (III$_B$) (PBL) | HIV-1 (BaL) (M/M) | FIV (CrFK) | MSV (C3H) |
| 1 | 0.9 ± 0.4 | 0.66 ± 0.19 | 0.34 ± 0.03 | 0.29 | 0.07 ± 0.02 | 0.002 ± 0.001 | 0.25 ± 0.01 | 0.16 ± 0.04 |
| 2 | 4.6 ± 3.1 | 3.0 ± 1.4 | 2.5 ± 0.3 | 2.9 | — | — | 0.97 ± 0.40 | 1.7 ± 0.9 |
| 11 | 1.9 ± 0.5 | 1.3 ± 0.4 | 3.0 ± 0.4 | 1.6 ± 0.6 | 0.12 ± 0.01 | 0.005 ± 0.0 | 0.66 ± 0.14 | 0.05 ± 0.01 |
| 4 | 1.4 ± 0.7 | 1.4 ± 1.2 | 1.9 ± 0.4 | 2.1 | — | — | — | 0.08 ± 0.03 |
| PMEA | 0.96 ± 0.24 | 1.9 ± 1.1 | 1.3 ± 1.1 | 1.9 | 0.55 ± 0.41 | 0.006 | 0.46 ± 0.19 | 0.62 ± 0.27 |
| (R)-PMPA | 0.36 ± 0.24 | 0.43 ± 0.41 | 0.46 ± 0.006 | 0.52 | 0.09 ± 0.03 | 0.003 ± 0.001 | 0.13 | 1.4 ± 0.9 |

TABLE 2-continued

| Cmpd Code | $CC_{50}^{b,c,d}$ ($\mu$g/ml) | | | | | |
|---|---|---|---|---|---|---|
| No. | CEM | MT-4 | PBL | M/M | CrFK | C3H |
| 1 | 11 ± 2.0 | 46 ± 7.4 | 2.2 ± 0.8 | >100 | 11 | >40 (200) |
| 2 | 64 ± 9.8 | ≧100 | — | — | 42 | >40 (200) |
| 11 | 62 ± 25 | ≧100 | 9.6 ± 2.5 | >100 | >100 | >40 (200) |
| 4 | 2.5 ± 0.2 | 10 ± 2.2 | — | — | — | ≧16 |
| PMEA | 16 ± 9.1 | 28 ± 12 | 1.7 ± 0.4 | >100 | 18 | >40 (200) |
| (R)-PMPA | 125 ± 26 | 72 ± 12 | >100 | >100 | >100 | >200 |

[a] 50% Effective concentration, or compound concentration required to inhibit HIV-induced cytopathicity (giant cell formation) in CEM and MT-4 cells, or p24 antigen production in PBL and M/M, or MSV-induced C3H cell transformation by 50%.
[b] 50% Cytostatic concentration, or compound concentration required to inhibit cell proliferation (CEM) or to reduce cell viability (MT-4, PBL, M/M) by 50%.
[c] Minimal inhibitory concentration, or compound concentration required to cause a microscopically visible alteration of cell morphology. The symbol ">" means that no visible toxicity could be recorded at the indicated concentration. The values between parentheses indicate the compound concentration at which morphological toxicity was observed.
[d] Data are the mean (±SD) of 2 to 4 separate experiments. Data without an SD value are the result of a single experiment carried out in duplicate.

TABLE 3

Effect of natural nucleosides and nucleobases on the antiviral activity of 6-PMEO and (R)-PMPO derivatives

| Cmpd Code No. | $EC_{50}^{a,b}$ ($\mu$g/ml) Upon addition of | | | | | |
|---|---|---|---|---|---|---|
| | as such | dThd (10 $\mu$M) | dCyd (1 mM) | Ado (400 $\mu$M) | Guo (10 $\mu$M) | Ade (100 $\mu$M) |
| 1 | 0.77 ± 0.25 | 0.35 ± 0.07 | 0.55 ± 0.35 | 0.63 ± 0.29 | 0.65 ± 0.21 | 0.26 ± 0.16 |
| 2 | 1.9 ± 0.75 | 1.4 ± 0.21 | 2.1 ± 1.7 | 4.4 ± 2.8 | 1.9 ± 0.49 | 3.3 ± 3.2 |
| 11 | 1.2 ± 0.25 | 0.83 ± 0.35 | 1.1 ± 0.51 | 1.5 ± 0.70 | 0.77 ± 0.38 | 0.35 ± 0.17 |
| 4 | 1.4 ± 0.71 | 1.0 ± 0.3 | 2.4 ± 1.9 | 1.4 ± 0.93 | 1.9 ± 0.92 | 1.7 ± 1.2 |
| PMEA | 0.94 ± 0.24 | 1.4 ± 0.4 | 2.1 ± 0.19 | 1.6 ± 0.4 | 1.0 ± 0.8 | 1.9 ± 1.3 |
| (R)-PMPA | 0.57 ± 0.26 | 0.43 ± 0.0 | 0.53 ± 0.26 | 0.46 ± 0.23 | 0.43 ± 0.0 | 1.6 ± 1.6 |
| PMEG | >0.05 | >0.25 | >0.25 | >0.05 | >0.05 | >0.05 |

[a] 50% Effective concentration, or compound concentration required to inhibit HIV-1 ($III_B$)-induced cytopathicity in CEM cell cultures.
[b] Data represent the mean (±SD) of at least 2 or 3 separate experiments.

TABLE 4

Anti-MSV activity of acyclic pyrimidine nucleoside phosphonates in newborn NMRI mice

| Compound | Dose (mg/kg)[a] | Total Number of Mice Used in the Experiments | Number of Mice not Developing a Tumor (percent) | Number of Long-Term Survivors (%) (>30 days) |
|---|---|---|---|---|
| 1 | 50 | 19 | 84 | 100[b] |
| (PMEO-2,4-di-$NH_2$-Pym) | 20 | 20 | 80 | 100 |
| | 8 | 18 | 44 | 89 |
| | 2 | 20 | 5 | 15 |
| 2 | 50 | 10 | 0 | 20 |
| (PMES-2,4-di-$NH_2$-Pym) | 20 | 10 | 0 | 20 |
| | 8 | 10 | 0 | 20 |
| | 2 | 8 | 0 | 0 |
| 11 | 20 | 10 | 20 | 40[c] |
| (PMPO-2,4-di-$NH_2$-Pym) | 8 | 20 | 15 | 40 |
| | 2 | 18 | 0 | 5 |
| PMEA | 100 | 10 | 100[d] | —[d] |
| | 20 | 29 | 89 | 94 |
| | 8 | 30 | 44 | 77 |
| | 4 | 20 | 5 | 35 |

TABLE 4-continued

Anti-MSV activity of acyclic pyrimidine nucleoside phosphonates in newborn NMRI mice

| Compound | Dose (mg/kg)[a] | Total Number of Mice Used in the Experiments | Number of Mice not Developing a Tumor (percent) | Number of Long-Term Survivors (%) (>30 days) |
|---|---|---|---|---|
| (R)-PMPA | 50 | 10 | 100 | 100 |
|  | 20 | 28 | 92 | 100 |
|  | 8 | 27 | 65 | 83 |
|  | 2 | 28 | 0 | 31 |

[a]Indicated drug dose given 2 hrs prior to MSV infection followed by 4 additional daily doses during the 4 subsequent days post infection. The mean day of tumor development in control MSV-infected mice was 4.5 days, whereas the mean day of animal death in the MSV-infected mice was 12.3 days.
[b]At the indicated drug dose (50 mg/kg), 16% of mice died prematurely (<24 days) likely due to toxicity of the drug and without signs of tumor formation. Premature death was not taken into account to calculate the percentage of long-term survivors.
[c]At the indicated drug dose (20 mg/kg), 50% of mice died prematurely (<6 days) likely due to toxicity of the drug and without signs of tumor formation. Premature death was not taken into account to calculate the percentage of long-term survivors.
[d]All mice died before day 6 likely due to toxicity of the drug. None of the mice showed tumor formation before death.

TABLE 5

Inhibitory activity of acyclic pyrimidine nucleoside phosphonate analogues against clinical HIV-1 isolates

| Compound Code Number | -Fold Resistance | | |
|---|---|---|---|
|  | HIV-1/L1S[b] | HIV-1/L6S[c] | HIV-1/L6S/PMEA[d] |
| 1 | 0.8 | 1.5 | 3.6 |
| 2 | 2.1 | 1.4 | 14 |
| 11 | 1.9 | 3.5 | 30 |
| PMEA | 2.0 | 2.7 | 7.3 |
| (R)-PMPA | 2.3 | 11 | 54 |

[a]Fold resistance measured against the laboratory HIV-1/III$_B$ strain in CEM cell cultures.
[b]Clinical isolate derived from a patient not related with NRTIs or ANPs and not containing NRTI- or ANP-specific mutations in the RT.
[c]Clinical isolate derived from a drug-treated patient. The RT contains the S68G, K70T, V75I, F77L, F116Y and Q151M mutations.
[d]HIV-1/L6S isolate cultured in the presence of PMEA and containing K65R in addition to the other NRTI-specific mutations as mentioned under c.

We claim:

1. A compound of the formula (I)

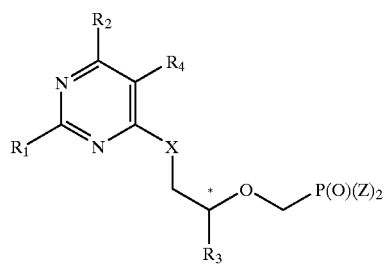

(I)

where $R_1$ is H, amino or methylsulfanyl;

$R_2$ is methyl, halo, —N($R_5$)$_2$, hydroxy, protected hydroxy or a group of the formula (Ia)

$$—X\underset{R_3}{\overset{*}{\diagup\!\!\!\diagdown}}O\diagdown\!\!\!\diagup P(O)(Z)_2$$ (Ia)

$R_3$ is independently H, methyl, hydroxymethyl, halomethyl or protected hydroxymethyl;

$R_4$ is H or halo;

X independently is oxygen, sulfur or a bond;

Z independently is hydroxy, an ester or amide;

$R_5$ is independently H, $C_1$–$C_8$ alkyl or a protecting group; and

* designates a chiral carbon atom; and salts and solvates thereof.

2. The compound of claim 1 wherein $R_1$ and $R_2$ are amino, $R_3$ is hydrogen and X is oxygen.

3. The compound of claim 1 wherein $R_1$ and $R_2$ are simultaneously amino, $R_3$ is methyl, X is oxygen and the $R_3$ configuration is (R).

4. The compound of claim 1 wherein $R_1$ and $R_2$ are simultaneously amino, $R_3$ is hydroxymethyl, X is oxygen and the $R_3$ configuration is (R).

5. The compound of claim 1 wherein $R_1$ and $R_2$ are simultaneously amino, $R_3$ is hydrogen and X is sulfur.

6. The compound of claim 1 wherein $R_1$ is amino, $R_2$ is hydroxy, $R_3$ is hydrogen and X is oxygen.

7. The compound of claim 1 which is crystalline.

8. The compound of claim 1 which is substantially pure enantiomer at the chiral carbon.

9. The compound of claim 8 which is in the (R) configuration.

10. The compound of claim 8 which is in the (S) configuration.

11. 2,4-diamino-6-[2-(phosphonomethoxy)ethoxy]pyrimidine.

12. 2,4-diamino-6-(R)-[2-(phosphonomethoxy)propoxy]pyrimidine.

13. 2-amino-4-hydroxy-6-[2-(phosphonomethoxy)ethoxy]pyrimidine.

14. 2,4-diamino-6-[(S)-3-hydroxy-2-(phosphonomethoxy)propoxy]pyrimidine.

15. 2,4-diamino-6-[(RS)-3-hydroxy-2-(phosphonomethoxy)propoxy]pyrimidine.

16. 2-amino-4-hydroxy-6-[(R)-2-(phosphonomethoxy)propoxy]pyrimidine.

17. 2-amino-4-hydroxy-6-[(RS)-3-hydroxy-2(phosphonomethoxy)propoxy]pyrimidine.

18. 2-amino-4-hydroxy-6-[(S)-3-hydroxy-2-(phosphonomethoxy)propoxy]pyrimidine.

19. 2,4-diamino-5-bromo-6-[2-(phosphonomethoxy)ethoxy]pyrimidine.

20. 2-amino-5-bromo4-hydroxy-6-[2-(phosphonomethoxy)ethoxy]pyrimidine.

21. A composition comprising a pharmaceutically acceptable excipient and a compound of claim 1.

22. A method of preparation of compounds of formula (I)

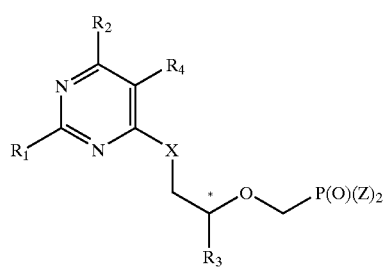

where $R_1$ is H, amino or methylsulfanyl;

$R_2$ is methyl, halo, —$N(R_5)_2$, hydroxy, protected hydroxy or a group of the formula (Ia)

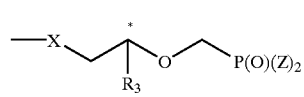

$R_3$ is independently H, methyl, hydroxymethyl, halomethyl or protected hydroxymethyl;

$R_4$ is H or halo;

X independently is oxygen, sulfur or a bond;

Z independently is hydroxy, an ester or amide;

$R_5$ is independently H, $C_1$–$C_8$ alkyl or a protecting group; and

* designates a chiral carbon atom; and comprising (a) reacting a compound of formula (II)

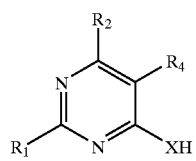

where $R_2$ is methyl, halo, —$N(R_5)_2$, hydroxy or protected hydroxy; and

X is O or S;

with a compound of the formula (III)

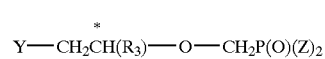

where

Z is an ester or an amide;

* designates a chiral carbon atom;

$R_3$ is H, methyl, halomethyl or protected hydroxymethyl; and

Y is a leaving group in dipolar aprotic solvent in the presence of a base.

23. The method of claim 22 further comprising isolating the resulting compound of the formula (I).

24. The method of claim 22 wherein Z is ester or amide and additionally hydrolyzing one or both Z groups to produce the compound of formula (I) where at least one Z is hydroxy.

25. The method of claim 22 where Z is $(OR_4)_2$ and $R_4$ is isopropyl.

26. The method of claim 22 where $R_3$ is methyl and Y is p-toluenesulfonyloxy.

27. A method for the preparation of compounds of formula (I)

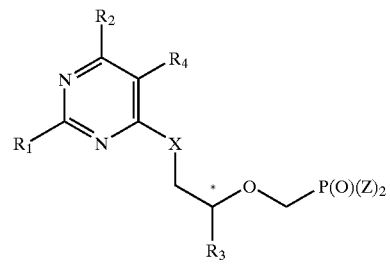

where $R_1$ is H, amino or methylsulfanyl;

$R_2$ is —$N(R_5)_2$;

$R_3$ is independently H, methyl, hydroxymethyl, halomethyl or protected hydroxymethyl;

$R_4$ is H or halo;

X is oxygen or sulfur;

Z independently is hydroxy, ester or amide;

$R_5$ is independently H, $C_1$–$C_8$ alkyl or a protecting group; and

* designates a chiral carbon atom comprising reacting a compound (IV)

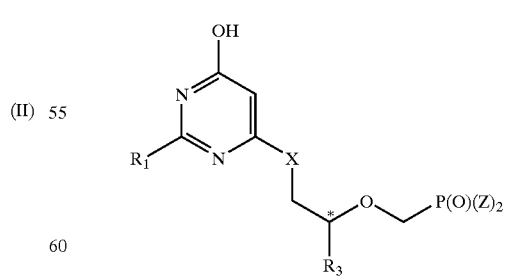

where $R_3$ is H, methyl, halomethyl or protected hydroxymethyl;

X is O or S; and

Z is amidate or ester;

with $N(R_5)_2$.

28. The method of claim 27 further comprising hydrolyzing one or both Z groups to produce the compound of formula (I) where one or both of Z are hydroxyl.

29. A method for preparation of compounds of formula (V)

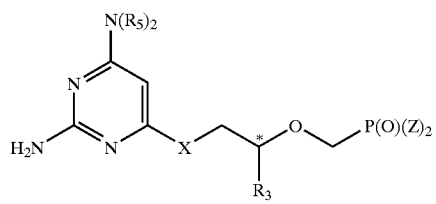

(V)

where

R$_3$ is H, methyl, hydroxymethyl, halomethyl or protected hydroxymethyl;

R$_5$ independently is H, C$_1$–C$_8$ alkyl or a protecting group;

X is oxygen or sulfur;

Z independently is hydroxy, an ester or amide; and

* designates a chiral carbon atom;

comprising reacting compound (IVa)

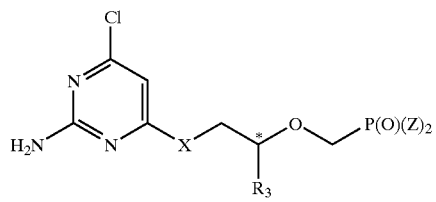

(IVa)

with N(R$_5$)$_2$ in anhydrous solvent, alkali hydroxide or alkali carbonate in aqueous solution.

30. A method of preparation of the compounds of formula (VI)

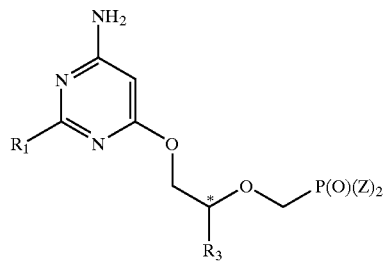

(VI)

where

R$_1$ is H, amino or methylsulfanyl;

R$_3$ is H, methyl, hydroxymethyl, halomethyl or protected hydroxymethyl;

Z independently is hydroxy, an ester or amide; and

* designates a chiral carbon atom;

comprising (a) reacting a compound of formula (VII)

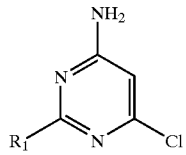

(VII)

where

R$_1$ is H, amino or methylsulfanyl with a compound of the formula (VIII)

(VIII)

where

Z is amide or ester in the presence of a base.

31. The method of claim 30 further comprising hydrolyzing Z group to produce a compound of formula (VI) where 1 or 2 Z groups are hydroxy.

32. A method of preparation of compounds of formula (XIII)

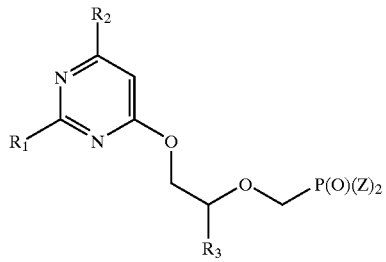

(XIII)

where

R$_1$ is H, amino or methylsulfanyl;

* is a chiral carbon atom;

R$_2$ is chloro, hydroxy or amino;

R$_3$ is H, methyl, halomethyl or hydroxymethyl;

Z is amide or ester comprising (a) reacting a compound of the formula (IX)

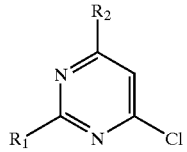

(IX)

where

R$_1$ is H, amino or methylsulfanyl;

R$_2$ is chloro or amino;

with a compound of the formula (X)

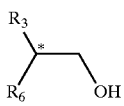
(X)

where
- $R_3$ is H, methyl, hydroxymethyl, halomethyl or protected hydroxymethyl;
- * is a chiral carbon atom;
- $R_6$ is hydroxy or protected hydroxy;
- or $R_3$ and $R_6$ are joined by a cyclic acetal or ketal protecting group;

in the presence of a base without solvent or in the presence of an aprotic solvent, to produce a compound of formula (XI)

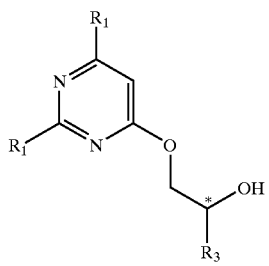
(XI)

where
- $R_1$ is H, amino or methylsulfanyl;
- * is a chiral carbon atom;
- $R_2$ is chloro or amino; and
- $R_3$ is H, methyl, halomethyl or protected hydroxymethyl; and (b) reacting compound (XI) with a compound of the formula (XII)

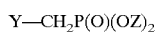
$Y—CH_2P(O)(OZ)_2$ (XII)

where
- Y is a leaving group;
- Z is amide or ester in the presence of a base in dimethylformamide or tetrahydrofurane to produce a compound of formula (XIII).

33. The method of claim 32 further comprising hydrolyzing Z group to produce a compound of formula (XIII) where 1 or 2 Z groups are hydroxyl.

34. A method of preparation of a compound of formula (I)

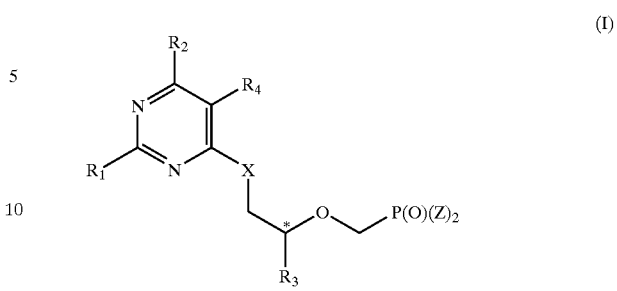
(I)

where
- $R_1$ is H, amino or methylsulfanyl;
- $R_2$ is amino;
- $R_3$ is H, methyl, hydroxymethyl, halomethyl or protected hydroxymethyl;
- $R_4$ is halo;
- X is oxygen;
- Z independently is hydroxy, an ester or amide; and
- * designates a chiral carbom atom;

comprising (a) reacting a compound of the formula (VI)

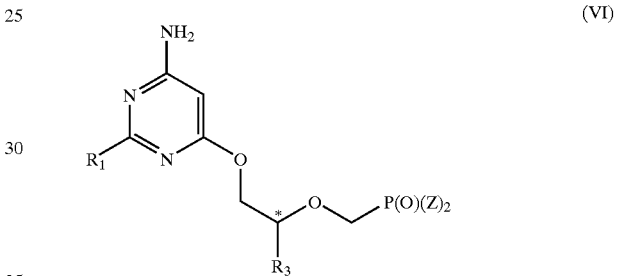
(VI)

where
- $R_1$ is H, amino or methylsulfanyl;
- $R_3$ is H, methyl, hydroxymethyl, halomethyl or protected hydroxymethyl;
- Z independently is an ester; and
- * designates a chiral carbon atom;

with elemental halogen in an inert solvent to produce a compound of formula (I).

35. The method of claim 34 further comprising hydrolyzing Z group to produce a compound of formula (I) where 1 or 2 Z groups are hydroxyl.

36. A method for the treatment of a viral infection comprising administering a therapeutically effective amount of a compound of claim 1 to a patient in need of such treatment.

37. The method of claim 36 where the virus is a DNA virus.

38. The method of claim 37 where the virus is a retrovirus or hepadnavirus.

39. A method for the treatment or prophylaxis of an HIV infection comprising administering a therapeutically effective amount of a compound of claim 1 to a patient in need of such treatment.

* * * * *